United States Patent
Pelssers et al.

(10) Patent No.: US 10,928,283 B2
(45) Date of Patent: Feb. 23, 2021

(54) SURFACE ANALYSIS DEVICE AND METHOD FOR ANALYSING ELASTICITY OF A RECEIVING SURFACE

(71) Applicant: KONINKLIJKE PHILIPS N.V., Eindhoven (NL)

(72) Inventors: Eduard Gerard Marie Pelssers, Panningen (NL); Cornelis Petrus Hendriks, Eindhoven (NL); Achim Hilgers, Alsdorf (DE); Mark Thomas Johnson, Arendonk (BE); Daan Anton Van Den Ende, Breda (NL); Roland Alexander Van De Molengraaf, Geldrop (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 115 days.

(21) Appl. No.: 16/323,546

(22) PCT Filed: Aug. 28, 2017

(86) PCT No.: PCT/EP2017/071510
§ 371 (c)(1),
(2) Date: Feb. 6, 2019

(87) PCT Pub. No.: WO2018/041761
PCT Pub. Date: Mar. 8, 2018

(65) Prior Publication Data
US 2019/0178764 A1 Jun. 13, 2019

(30) Foreign Application Priority Data

Aug. 31, 2016 (EP) .................................. 16186693

(51) Int. Cl.
*G01N 3/08* (2006.01)
*G01N 3/00* (2006.01)
*A61B 5/00* (2006.01)

(52) U.S. Cl.
CPC ............. *G01N 3/08* (2013.01); *A61B 5/0053* (2013.01); *A61B 5/442* (2013.01); *G01N 3/00* (2013.01);
(Continued)

(58) Field of Classification Search
None
See application file for complete search history.

(56) References Cited

U.S. PATENT DOCUMENTS

| 5,879,312 A | 3/1999 | Toshiyuki |
| 6,564,640 B1 | 5/2003 | Allaei |

(Continued)

FOREIGN PATENT DOCUMENTS

| EP | 1081235 A2 | 3/2001 |
| EP | 1340002 B1 | 12/2004 |

(Continued)

OTHER PUBLICATIONS

Y. Shi et al "An Analytic Model for Skin Modulus Measurement Via Conformal Piezoelectric Systems" ASME J. Appl. Mech. 2015 82(9).

(Continued)

*Primary Examiner* — Natalie Huls
*Assistant Examiner* — Jermaine L Jenkins
(74) *Attorney, Agent, or Firm* — Schott, P.C.

(57) ABSTRACT

The invention provides a surface analysis device for application to a receiving surface to enable analysis of at least one measure of an elasticity of said surface across multiple different linear stretches or sections of the surface. The device includes a two-dimensional arrangement of actuators (Continued)

and sensors, comprising at least one actuating element, at least one sensing element, and at least one further sensing or actuating element. Selected sets of two or more of these elements are activated together by a controller, each set including at least one actuator and one sensor, to thereby obtain a measure of elasticity between each actuator and sensor pair in the set. Elasticity measures are obtained based on stimulating a deformation in the receiving surface at the actuator site, and measuring a resultant pressure and/or force exerted by the receiving surface at a further displaced point. Sensors may monitor a change in the exerted pressure and/or force for example.

21 Claims, 9 Drawing Sheets

(52) U.S. Cl.
CPC . *A61B 2562/0247* (2013.01); *A61B 2562/046* (2013.01); *G01N 2203/0017* (2013.01); *G01N 2203/0075* (2013.01); *G01N 2203/0282* (2013.01)

(56) References Cited

U.S. PATENT DOCUMENTS

| 10,309,377 | B2* | 6/2019 | van den Ende | H01L 41/0926 |
| 2010/0168592 | A1 | 7/2010 | Kang et al. | |
| 2010/0234779 | A1* | 9/2010 | Asvadi | A61H 1/02 601/84 |
| 2014/0180171 | A1 | 6/2014 | Hyde et al. | |
| 2014/0352448 | A1 | 12/2014 | Shih et al. | |
| 2015/0216758 | A1 | 8/2015 | Ajiki et al. | |

FOREIGN PATENT DOCUMENTS

| EP | 2901999 A1 | 8/2015 |
| JP | S60-90536 A | 5/1985 |
| JP | 2014-038089 A | 2/2014 |
| WO | 2014/100092 A1 | 6/2014 |

OTHER PUBLICATIONS

A. Vinckier et al "Measuring elasticity of biological materials by atomic force microscopy" FEBS letters, vol. 430, Issues 1-2, Jun. 23, 1998, pp. 12-16.

Bo Qiang et al "Estimation of skin elasticity by measuring surface wave velocity under impulse stimulus using compact optical sensors". Coll. of Med., Dept. of Physiol. & Biomed. Eng., Mayo Clinic Coll. of Med., Rochester, MN, USA. Ultrasonics Symposium (IUS), 2009 IEEE International, Sep. 20-23, 2009. p. 185-188, E-ISBN 978-14244-4390-1.

Grant Kruger et al , "Skin Hardness and Elasticity Measurement Device". ME 450 Fall 2010 , Dec. 15, 2010. University of Michigan.

* cited by examiner

SURFACE ANALYSIS DEVICE AND METHOD FOR ANALYSING ELASTICITY OF A RECEIVING SURFACE

CROSS-REFERENCE TO PRIOR APPLICATIONS

This application is the U.S. National Phase application under 35 U.S.C. § 371 of International Application No. PCT/EP2017/071510, filed on Aug. 28, 2017, which claims the benefit of EP Patent Application No. EP 16186693.4, filed on Aug. 31, 2016. These applications are hereby incorporated by reference herein.

FIELD OF THE INVENTION

This invention relates to a surface analysis device and method for determining measures of elasticity of a receiving surface, and in particular determining measures corresponding to multiple directions across the receiving surface.

BACKGROUND OF THE INVENTION

Analysis of elasticity of surfaces is of importance in many different industries and technical areas. By way of example, any application in which a fabric, textile or other material is utilised for a technical function may benefit from the capacity to assess elasticity of a surface of the material in a detailed manner. This may be to identify functional technical parameters of a component, or to assess likely lifetime or durability of components or products. Examples include analysis of textiles used in furnishings or clothing for instance, or of components used as force transfer parts (such as belts) in machinery.

In addition, one further area in which surface analysis is of particular interest is that of analysis of skin.

Skin performs multiple functions critical for the human body. These include regulation of body temperature and protection from water loss. There are measurable properties of skin directly related to these functions—namely elasticity and hardness. It is known that these properties are directly affected by chronological ageing and photo-ageing, and also that the degree of effect varies for different areas on the body.

The ability to quantify these properties is important, since it enables a characterisation of the aged status of a person's skin, which in turn can help in determining appropriate and effective skin-healing therapies to repair any damage.

Tools for assessing skin elasticity and hardness is hence an on-going area of interest. In particular, tools for determining skin indentation resistance and also skin stretching capacity are of significant interest.

Various methods and approaches exist for evaluating skin elasticity and hardness in a laboratory setting. These include Atomic Force Microscopy and tissue electrography. While these have proved effective in providing tissue elasticity measures, they currently require complicated equipment which would be in appropriate for use in clinical or home settings. This limits their applicability, and requires that potential patients (or other users) must visit dedicated laboratories staffed by trained operators to achieve evaluations of the status of their skin. This is simply not practicable or scalable for large numbers of patients. Of interest are devices capable of providing measures of skin elasticity in a clinical and home setting.

Some devices do exist which are more applicable to a non-laboratory setting. These include the 'Cutometer MPA 580' sold by Courage and Khazaka electronic. This device is more practical, but nonetheless remains a relatively large and complex machine, which is unsuitable for miniaturisation and integration into a small-scale treatment and/or measurement device for example. Small-scale device offer far greater practicality and usability and hence are of significant interest.

Certain approaches do exist which are more applicable to small-scale or miniaturised devices. In particular, these approaches are typically based on the application of in-plane or out-of plane deformations to a point on a user's skin, and measurement of a corresponding reaction force exerted by the skin at ether the same point or a different, spatially displaced point.

US 2014/0352448 for example discloses a Piezoelectric Finger sensor capable of measuring both the Young's Modulus and shear modulus of a sample of tissue at given a single point. The finger sensor includes two layers of piezoelectric material, one configured to deform to apply a force to the sample of tissue, and another configured to sense a displacement of the first layer. By monitoring the sensed displacement value, a resistance force of the skin can be determined, and hence an elasticity of the skin at the given point evaluated. A plurality of these devices may be applied to a user's skin to determine elasticity values at a plurality of different individual points.

While this approach is far more practical, it is limited to obtaining elasticity measurements at single isolated points only. There is no disclosed means for obtaining measures of elasticity across an extended length of tissue for instance, or for obtaining measures corresponding to different sample lengths, extending in different directions. Directional data is highly valuable in the present context, since it is known that skin in particular exhibits anisotropy effects in its elasticity, information about which would enable far more detailed and accurate characterisation of the state of ageing of skin.

A paper by Y. Shi et al (Shi Y Y et al. An Analytic Model for Skin Modulus Measurement Via Conformal Piezoelectric Systems. ASME. *J. Appl. Mech.* 2015; 82(9)) discusses an analytical model for determining the Young's modulus of a sample of skin based upon deforming skin at a first point, and measuring a resultant pressure or force applied by the skin at a second, spatially displaced point. The approach uses a linear arrangement of three PZT ribbons applied to a layer of skin, one of which is electrically stimulated to contract, thereby inducing a consequent expansion of the other two ribbons as a result of consequent deformation of the intervening skin tissue. The extent of this expansion is measured and a Young's modulus thereby calculated.

While this approach enables measurement of skin elasticity across an extended length of tissue (extending between the various ribbons), it is highly limited in its practical applicability. In particular, it provides no means for obtaining multiple measures of elasticity corresponding to different lengths or regions of skin. Although sensor measurements are taken at a plurality of distances from the contracting ribbon, the model assumes a constant and common elasticity at every sensor location. It does not allow for detection and measurement of variations in elasticity occurring at different linear locations.

The model also, as in the previous case, provides no means for obtaining multi-directional data. The model is entirely premised on an exclusively linear arrangement of ribbons, and provides no indication for how the approach could be expanded to provide multi-directional measures.

Finally, there exists a further device manufactured by Courage and Khazaka electronic, which is designed to measure the direction of collagen and elastin fibres in the skin. It is based on measuring the resonance running time of an acoustical shockwave through skin. The device comprises a single actuator, configured to generate the shockwave, and a single sensor configured to detect arrival of the shockwave. The device can be manually rotated to enable analysis of collagen and elastin fibre directionality in a number of different skin directions.

The device is of limited applicability to measuring skin elasticity per se, and again provides capacity for measuring skin properties across only a single directional length of skin at any one time.

SUMMARY OF THE INVENTION

There is a general need in the art therefore for improved devices for analysing surface elasticity, maintaining small form factor and simple operation, but capable of providing a greater quantity and range of different measurement data, in a straightforward manner, to thereby enable a more detailed and insightful analysis of a given surface of interest.

It is an object of the invention to address the need at least partially. This object is achieved with the invention as defined by the independent claims. The dependent claims define advantageous embodiments.

According to an aspect of the invention, there is provided a device for application to a receiving surface to analyse an elasticity of said receiving surface across a plurality of different linear sections of said surface, the device comprising a carrier, having a surface;

an arrangement of three or more surface interaction elements mounted to the carrier surface, each element being operable to perform only one of an actuation or pressure sensing function at any one time, and the elements being spatially separated from one another and distributed in two dimensions across the carrier surface, and wherein the arrangement includes at least a first surface interaction element operable to perform an actuation function and at least a second surface interaction element operable to perform a pressure sensing function; and a controller, operatively coupled with the surface interaction elements, and adapted to:

control the first surface interaction element to induce a deformation in the receiving surface at a first contact point, control the second surface interaction element to measure a pressure and/or force exerted by the receiving surface at a second, spatially separated, contact point, to enable determination of a measure of an elasticity of the receiving surface between the first and second points, and control one or more further surface interaction elements to either induce a deformation in, or measure a pressure and/or force exerted by, the receiving surface at a further one or more contact points, in order thereby to enable determination of a measure of elasticity between each of said further one or more points, and either the second or first contact point.

Such a device can thus be designated a surface analysis device based on its capability to analyse an elasticity of said receiving surface across a plurality of different linear sections of said surface.

Embodiments of the invention are hence based on the application of a plural array (or arrangement) of sensors and actuators to a target area of a given receiving surface. Each actuator is operable to apply a force to the receiving surface to induce some deformation at a given point, or across some small given area. Each sensor is operable to measure a force or pressure applied to it by the receiving surface at a separate given point. By monitoring or otherwise determining a change in the measured force or pressure at a given sensor point following application of a deformation by a given actuator at the separate point, a measure of the surface stiffness between the actuator and the sensor may be obtained. In particular, the stiffer the intervening section of receiving surface, the greater will be the measured change in pressure or force at the sensor.

By activating different combinations of actuators and sensors within the array, a measure of the stiffness of the skin (or other target receiving surface) across multiple different linear stretches or sections of the skin can be obtained. This allows for a richer and more detailed analysis of skin elasticity. In some cases, multiple measurements may be obtained simultaneously. In other cases, multiple measurements may be obtained individually or sequentially.

The arrangement may be designed or configured to follow any desired pattern or layout. The larger or more complex the provided pattern, the greater the variety and breadth of different measurements that can be obtained across a target area of a receiving surface.

Furthermore, the arrangement of surface interaction elements extends laterally across two-dimensions, and hence includes actuators and sensors displaced from one another at a variety of different angles. By selectively activating different combinations of these, data pertaining to elasticity along multiple different directions can be obtained. As discussed above, multi-directional data is highly valuable since it enables analysis of anisotropy effects. These can provide a more detailed insight into the current state of a person's skin.

In the simplest case, the arrangement comprises at least three surface interaction elements which includes at least one capable of performing each of actuation and sensing. At least one further surface interaction may be operable to perform either actuation or sensing. The controller is adapted to control the at least one further element simultaneously with one or both of the first or second, depending upon which function (actuation or sensing) it is configured to perform. If it is operating as a sensor, it may be activated to measure a pressure and/or force concurrently with activation of the first (actuation) element. If it is operating as an actuator, it may be controlled to operate concurrently with the second (sensing element). Alternatively, where more than three elements are provided, each further element may be activated concurrently with at least one of the other further elements, the other further element being adapted to perform an opposite function (of actuation and sensing).

In either case, one element of the arrangement (either the first or second) is effectively 'shared' between at least two other elements for the purposes of performing elasticity analysis. This enables two separate measures of elasticity to be obtained (for different intervals, sections or stretches of skin) using only three elements (rather than, for example, two dedicated pairs of two). This confers significant benefits in terms of operational efficiency, as well as in minimising form factor.

In more sophisticated examples, more than three surface interaction elements may be provided, arranged according to any desired pattern or configuration. In each case however, at least one element of the arrangement is applied to provide some multiple measurement capability: at least one element provides measurements in combination with multiple of the other elements. In this way, the invention achieves efficient sharing of surface interaction resources, and maximises the density of data that can be obtained over a given sample surface area.

The receiving surface may be an area of skin, although the invention is not limited to use with skin. Embodiments may usefully be applied to analysis of any flexible or compliant area of material. In the descriptions that follow, explanations provided in terms of use with skin should be interpreted as exemplary only, and in each case the concept described may be applied equally to any other flexible receiving surface.

Embodiments include an arrangement of surface interaction elements, each element operating for the purposes of a given measurement as either a sensor or an actuator. Some elements may have a fixed operation: operating always as a sensor or always as an actuator. Some elements may be operable in either mode. However, none is controlled to operate as both simultaneously.

By requiring that each surface interaction element perform only one of an actuation or sensing at once, measurement of elasticity across lateral stretches of the receiving surface between different points is more readily achievable. On the contrary, simultaneous actuation by a given sensing element would fundamentally distort any lateral elasticity measurement being made. The local deformation caused by this actuation at the sensing element would almost entirely saturate the force measurements made, rendering it difficult or impossible to accurately measure any lateral elasticity between a sensor and a laterally displaced actuator.

Each actuator-sensor pair enables determination of a measure of elasticity of the receiving surface between that pair. The phrase 'measure of elasticity' is intended broadly to refer generally to any value, trend or relationship for instance which provides an indication or representation of a receiving surface elasticity. By elasticity is meant generally, a stiffness, hardness, firmness, or compliancy. This term is not intended to limit the invention to any particular scientific or academic definition of elasticity (the invention is not limited for example to enabling measure of a Young's Modulus of a receiving surface, although this may be possible using certain embodiments).

Embodiments of the invention are directed to the use of a plural arrangement of actuators and sensors to obtain multiple different measures of elasticity, corresponding to different areas, linear sections or directions across the receiving surface, and optionally corresponding to different kinds of elasticity measure (e.g. shear elasticity or compressional elasticity). The term 'linear section' refers to any linear interval along the surface, extending between two respective points on the surface. It refers to a stretch or length or distance of skin between two points. In this respect two different linear sections may overlap, but differ for example in either their direction or their specific length.

Each embodiment makes use of a plural set of at least three surface interaction elements to capture at least two elasticity measurements. In some cases, these two measurements may be obtained simultaneously, in other cases they may be obtained individually or sequentially.

According to at least one set of embodiments for instance, the controller may be operable to selectively control a plurality of different pairs of the surface interaction elements, each pair including one element operable to perform actuation and one element operable to perform pressure and/or force sensing, to independently or simultaneously perform respective pairs of surface-deformation and pressure/force sensing functions, to thereby enable a plurality of independent or simultaneous elasticity measures across a plurality of different linear sections of said receiving surface.

Each pair in this arrangement consists of a single actuator and a single sensor, separated by a different particular linear stretch of the receiving surface. Each pair is operable to achieve an individual measure of the surface elasticity, corresponding to the particular linear stretch of receiving surface extending between them.

The pairs may overlap, such that a single element contributes to achieving the measurement for a plurality of different linear surface sections. Where the shared element is an actuator, a plurality of measurements may be obtainable in this way simultaneously.

Wherein the actuator is a sensor, each individual measurement may be performed sequentially.

According to a further set of example embodiments,
a plurality of the surface interaction elements may be operable to perform an actuation function, and wherein the controller is adapted to control said plurality of elements to induce respective deformations in the receiving surface at a respective plurality of contact points, and to control a single further surface interaction element to measure a pressure and/or force exerted by the receiving surface at a further spatially displaced contact point; and/or a plurality of the surface interaction elements may be operable to perform a pressure and/or force sensing function, and wherein the controller is adapted to control a single further surface interaction element to induce a deformation in the receiving surface at a single contact point, and to control said plurality of surface interaction elements to measure a pressure and/or force exerted by the receiving surface at a further plurality of contact points.

In particular, in either case, the plurality of surface interaction elements may each be positioned adjacent to said single surface interaction element (i.e. with no further elements situated in-between). There may be provided for example a single central actuator surrounded by a plurality of sensors, or a single central sensor surrounded by a plurality of actuators. Alternatively, the plurality of elements may be aligned linearly, and the single reciprocal element positioned at a location laterally displaced from that line for example.

There is hence provided in each of these example embodiments a plural set of actuators in combination with a single sensor, or a plural set of sensors, in combination with a single actuator. Between the single provided element and each of the plurality of reciprocating elements is a different particular linear stretch of the receiving surface. Where each of the plurality are positioned adjacent to the single element (i.e. with no elements lying in-between), then each of these different linear stretches also extends in a different angular direction.

Each embodiment allows for a plurality of elasticity measurements to be performed, one for each of said different linear stretches of the receiving surface lying between each of the plurality of elements and the single reciprocal element.

Such an arrangement carries the advantage of enabling a plurality of different measurements to be performed while minimising the required number parts. Since a single sensor or single actuator can be paired respectively with each of a plurality of further reciprocal elements, this avoids the need to provide a separate dedicated actuator-sensor pair to perform each measurement. The single sensor or actuator is effectively shared between each of the plurality of reciprocating actuators or sensors, and hence only one is required. This reduces costs of the device, and also minimises the required form factor for achieving a given number of different measurements.

Depending upon the size of the overall arrangement of surface interaction elements, the arrangement may include either one or both of the above described configurations in particular embodiments. Furthermore, either of these arrangements or operation modes may be combined together with the previously described operation mode in which pairs of actuators are simultaneously or separately activated.

According to one or more sets of embodiments, at least a subset of the surface interaction elements may be operable to each perform a selected one of either actuation or pressure sensing. This provides considerable flexibility and adaptability in the operation of the device.

In particular, according to these embodiments, the controller may be operable to selectively switch each of said at least subset of surface interaction elements between performing an actuation function and a sensing function.

This allows the configuration of the surface interaction elements to be adapted and altered at will to provide any arbitrary combination of actuators and sensors. This in turn enables a broader selection and variety of different elasticity measurements to be obtained. By selectively switching different combinations of elements between actuation and sensing functionalities, different stretches of the receiving surface, extending in different directions for example and/or corresponding to different distances or lengths, can be analysed.

Additionally, this flexibility may allow for multiple different measures of elasticity to be gathered across a single given linear stretch of a receiving surface. Different elasticity measures may require different configurations or combinations of actuators and sensors to achieve. Where the operation of surface interaction elements is alterable, a multiplicity of these different measures may in examples be achieved over the same given area or section of the receiving surface.

According to this or any other embodiment of the invention, at least a subset of the surface interaction elements may comprise an electroactive polymer material adapted to deform in response to application of an electrical signal, and/or adapted to generate an electrical signal in response to a force or pressure exerted on the element.

Electroactive polymer materials enable in particular simultaneous actuation and sensing capabilities through superposing high magnitude DC signals with low amplitude AC signals. The high amplitude DC signal induces a static deformation, while the low-amplitude AC signal enables pressure sensing by means of monitoring capacitance changes.

In embodiments, the surface interaction elements may be adapted to operate according to different modes. In particular, the actuators may be adapted either to induce in-plane deformations in the receiving surface (stretching) and/or to induce out-of-plane deformations (indentations) in the receiving surface. The sensors likewise may be adapted to detect or sense one or both of in-plane or out of plane pressure or force. These different modes may allow for different measures of elasticity to be obtained.

More particularly, according to one or more embodiments, controlling of the surface interaction elements may include:

controlling at least one surface interaction element to induce an out-of plane deformation in the receiving surface at a respective contact point, and controlling at least a further surface interaction element to measure an out-of-plane pressure and/or force exerted by the receiving surface at a further respective contact point; and/or controlling at least one surface interaction element to induce an in-plane deformation in the receiving surface at a respective contact point, and controlling at least a further surface interaction element to measure an in-plane or out-of-plane pressure and/or force exerted by the receiving surface at a further respective contact point.

By in-plane is meant in a direction predominantly or substantially parallel with the receiving surface. By out-of-plane is meant in a direction predominantly or substantially perpendicular or normal to the receiving surface.

These different modes of surface manipulation and sensing may enable provision of different measures of surface elasticity. In particular, the first mode or configuration enables a measure of indentation resistance to be achieved. By inducing an out-of-plane deformation (indentation) at a first point, and monitoring an out-of-plane pressure or force exerted by the surface at a laterally displaced point, the resistance of the surface to indentation can be measured. The stiffer the resistance, the greater a measured drop in pressure at the sensor. The weaker the resistance, the smaller a measured drop in pressure at the sensor.

Additionally, where two actuators are provided surrounding a single sensor, and both actuators are controlled to induce a simultaneous out-of-plane deformation, a measure of a convolution of a stretching capacity (or lateral/interfacial elasticity) and an indentation resistance can be obtained at the central sensor.

According to at least one or more examples, a time-varying out-of-plane deformation may also be generated in some cases. This enables dynamic measures of elasticity to be determined.

The second mode or configuration allows, according to one or more examples, measurement of a stretching capability (interfacial or shear elasticity). The second mode also allows, according to one or more embodiments, measurement or evaluation of a wrinkle size or position. By applying a lateral deformation and determining the extent of actuation required before a sensor response is activated, an estimated size of a wrinkle lying in-between the actuator and sensor can be determined.

The second mode also allows for further measurement capability in the case that a time-varying in-plane deformation is induced.

In particular, according to at least one set of embodiments, at least one surface interaction element may be operable to induce an in-plane deformation, and at least a further surface interaction element may be operable to measure an in-plane or out of plane pressure and/or force, and wherein the controller is adapted to apply a time-varying control signal to said at least one element in order to control the at least one element to induce a time-varying in-plane deformation in the receiving surface, and is further adapted to determine, based on an output from the further surface interaction element, a time delay between generation of the time-varying deformation and detection of a pressure or force change at the further element.

The time-varying deformation induces a surface acoustic (Lamb) wave to propagate across the receiving surface, which can be detected by a pressure or force sensor spaced at a certain distance apart from the actuator. By measuring the time delay between generating the wave and its being detected by the sensor, a velocity of the wave can be determined. From this, a measurement of skin elasticity can be calculated. For skin in particular, the speed of the Lamb wave enables a skin viscoelasticity to be determined.

According to one or more embodiments, at least one surface interaction element may be operable to induce both an in-plane and out-of plane deformation simultaneously, and wherein the controller is further adapted to control said at least one surface element to induce a non-time-varying out of plane deformation in the receiving surface.

The non-time varying out of-plane deformation applies a static (baseline) pressure to the receiving surface, while the time-varying in-plane deformation generates surface acoustic waves (shear waves). By changing the out-of-plane deformation level, the static baseline pressure at which the shear waves are generated may be changed. This provides a further degree of freedom to the system, and may provide a further level of depth to the gathered data, enabling a more detailed picture of elasticity to be obtained.

Alternatively, changing the static out-of-plane deformation may enable adjustment of a coupling of the surface interaction element with the receiving surface.

The simultaneous in-plane and out-of plane deformations may be achieved by a number of different particular means. An EAP-based actuator may advantageously be applied, wherein a low-amplitude AC signal is superposed on high magnitude DC signal. The DC signal generates the out of plane deformation. The AC signal generates the time-varying in-plane deformation.

A dielectric elastomer may for example be used, or a PVDF-based relaxor polymer.

According to at least one set of embodiments, the controller may be operable to control a first surface interaction element to induce an out-of-plane deformation in the receiving surface, and to control at least a further surface interaction element to measure an out-of-plane pressure and/or force exerted in a direction towards the receiving surface, and optionally wherein the controller is adapted to control two surface interaction elements to induce respective out-of-plane deformations in the receiving surface, the further surface interaction element being positioned in-between said two elements.

According to this set of embodiments, the sensor is adapted to measure a pressure or force exerted by the receiving surface in a direction toward the receiving surface, i.e. effectively a pulling force being applied to the sensor.

This embodiment enables determination of a measure of skin friction or adhesion. Deformation of the skin causes a pulling or peeling of the skin away from the sensor. Where there is low skin adhesion or friction, there will be low or even zero pulling force exerted on the sensor; the skin will simply come away from the sensor. Where there is high adhesion/friction, there will be high force exerted while the skin is being separated, followed by zero force once the skin has separated.

According to one or more embodiments, one or more of the surface interaction elements may be further operable to perform a temperature sensing function, and wherein the controller is adapted to control said element to measure a temperature of the receiving surface, and optionally wherein the device further comprises a heating element operable to heat the surface interaction element and/or a portion of the receiving surface.

It is known that temperature has an effect on material elasticity. These embodiments allow for elasticity measurements to be corrected for temperature if necessary.

Additionally, where a heating element is provided, a systematic assessment of skin elasticity at different temperatures can be performed. The behaviour of skin as a function of temperature provides a richer data-set than measurement at a single temperature alone.

Temperature sensing may also be employed in embodiments in determining thermal properties of skin. This may enable for instance identification of the position of an artery or other anatomical feature below the surface. This may assist in positioning of the device for optimal measurements of a particular region of interest.

According to one or more embodiments, the carrier may be a compliant carrier for conforming to a topology of the receiving surface. In these cases, the carrier is adapted to shape compliantly to the contours of the receiving surface to which it is applied. This improves efficacy of the device by ensuring that all of the surface interaction elements are uniformly applied to the receiving surface with minimal separation distance.

In accordance with at least a set of embodiments, the device is for application to skin. In these cases, the carrier may be flexible for molding to the surface contours of the skin receiving surface. The carrier should also preferably be formed of a locally compressible material, to provide a soft, comfortable feel for users of the device. The carrier in particular examples may be configured for forming part of a wearable device, the device arranged in use to hold the carrier securely against the skin of the user.

According to a further aspect of the invention, there is provided a method of determining a measure of elasticity of a receiving surface across a plurality of differently linear sections of said receiving surface, by means of a surface analysis device, the surface analysis device comprising:

a carrier, having a surface; and an arrangement of three or more surface interaction elements mounted to the carrier surface, each element being operable to perform only one of an actuation or pressure sensing function at any one time, and the elements being spatially separated from one another and distributed in two dimensions across the carrier surface, and wherein the arrangement includes at least a first surface interaction element operable to perform an actuation function and at least a second surface interaction element operable to perform a pressure sensing function;

the method comprising:

controlling the first surface interaction element to induce a deformation in the receiving surface at a first contact point, controlling the second surface interaction element to measure a pressure and/or force exerted by the receiving surface at a second, spatially separated, contact point, to enable determination of a measure of an elasticity of the receiving surface between the first and second points, and controlling one or more further surface interaction elements to either induce a deformation in, or measure a pressure and/or force exerted by, the receiving surface at a further one or more contact points, in order to enable determination of a further measure of elasticity between each of said further one or more points, and either the second or first contact point.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a surface analysis device for application to a receiving surface to enable analysis of at least one measure of an elasticity of said surface across multiple different linear stretches or sections of the surface. The device includes a two-dimensional arrangement of actuators and sensors, comprising at least one actuating element, at least one sensing element, and at least one further sensing or actuating element. Selected sets of two or more of these elements are activated together by a controller, each set including at least one actuator and one sensor, to thereby obtain a measure of elasticity between each actuator and sensor pair in the set. Elasticity measures are obtained based on stimulating a deformation in the receiving surface at the actuator site, and measuring a resultant pressure and/or force exerted by the receiving surface at a further displaced point. Sensors may monitor a change in the exerted pressure and/or force for example.

Figure 1:
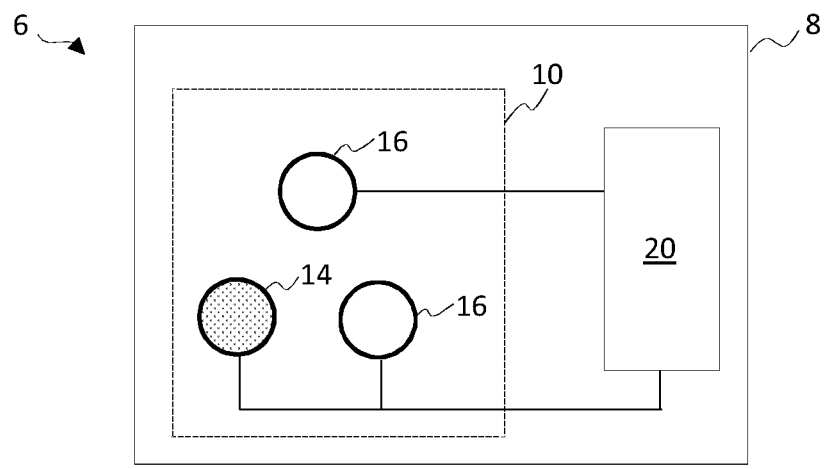
FIG. 1 schematically depicts an example surface analysis device in accordance with the invention.

A first basic example of a surface analysis device 6 in accordance with the invention is illustrated in FIG. 1. The device comprises a carrier 8, to which is mounted an arrangement 10 of surface interaction elements 14, 16 and a controller 20, the controller being operatively coupled with the elements.

For the example of FIG. 1, an arrangement 10 of three surface interaction elements is provided, which includes one element 14 operable to perform an actuation function and two elements 16 operable to perform pressure and/or force sensing functions. The elements are arranged spatially separated from one another and form a triangle configuration.

Although an arrangement of one actuator and two sensors is provided in this example by way of illustration, in alternative examples, one sensor and two actuators may alternatively be provided.

Additionally, the arrangement of three surface interaction elements 14, 16 represents only a simplest first example of a possible configuration. In further examples, the arrangement may be expanded, and may include any number of different surface interaction elements, arranged in any desired pattern or configuration. A broader arrangement allows for a greater variety of different elasticity measurements to be obtained, corresponding to a greater number of different sections of the receiving surface for example, or corresponding to different particular measures or metrics of elasticity. More detailed examples of further possible arrangements and corresponding operation modes will be described in more detail in passages to follow.

The carrier 8 is adapted to be applied to a region of a receiving surface, such that the surface interaction elements are each inversely applied or pressed against a respective point or area on the receiving surface (a respective contact point). This receiving surface may be skin for example (although the invention is by no means limited to use with skin). In examples, the controller may be embedded within the body of the carrier, or otherwise covered by a flexible shielding layer, such that the controller is not pressed against the receiving surface upon application of the carrier. This might interfere with operation of the device for example or may be uncomfortable in the case that the device is applied to a user's skin.

The surface interaction elements may also each be covered or shielded by a flexible covering layer, either to protect the element, or to improve device comfort for instance. The covering layer may be an insulator, to protect against any electrical leakage or conduction from the elements to a user's skin.

The carrier may be in the form of a thin, flexible patch or pad for easy application and/or adhesion to a user's skin. Such a patch or pad should be flexible, to allow for robust and even coupling with a user's skin, but should also retain sufficient rigidity to resist deformation by the actuator(s).

In operation, the controller 20 may be adapted to control the actuating element 14 to induce an (in-plane or out-of plane) deformation in the receiving surface at a point or area of the surface lying directly beneath it. Concurrently with activation of the actuating element 14, or at least while activation of this element is still on-going, the controller may be adapted to further control one or both of the sensing elements 16 to measure or monitor a pressure and/or force exerted upon them by an area or point of the receiving surface situated beneath them. By measuring and/or monitoring this pressure and/or force, a measure of an elasticity (or stiffness) of the section or stretch of the receiving surface lying between the actuating element 14 and each respective sensing element 16 may be obtained.

In particular, controller may control the sensing elements to monitor a pressure and/or force over time, such that changes in pressure or force can be identified. Outputs of the sensing elements may be monitored both before and after activation of the actuator, such that changes in pressure arising as a result of deformation of the receiving surface (by the actuating element) can be identified.

The magnitude of the experienced changes in pressure or force is dependent on the elasticity or stiffness of the intervening material. In particular, where the section of receiving surface lying between the actuating element and a respective sensing element is relatively stiff, it is expected that a change in pressure or force experienced by the sensing element will be relatively greater. Likewise, where the section of surface is less stiff, it is expected that any change in force or pressure at the sensor will be smaller.

By evaluating or comparing measured pressure and/or force values (or measured changes in these values) against a standard reference set of values, a corresponding measure of elasticity may be obtained. Alternatively a physical model may be applied to calculate a corresponding elasticity measure based on detected sensor outputs, or changes in said detected outputs.

In accordance with at least one set of advantageous embodiments, the actuating elements 14 and/or the sensing elements 16 may be formed using an electroactive polymer material. Electroactive polymers (EAPs) are an emerging class of materials within the field of electrically responsive materials. They can work as sensors or actuators and can be easily manufactured into a variety of shapes allowing easy integration into a large variety of systems.

Advantages of EAPs include low power, small form factor, flexibility, noiseless operation, accuracy, the possibility of high resolution, fast response times, and cyclic actuation. Materials in this field have undergone significant development over the last ten years, and various characteristics such as actuation stress and strain have improved considerably. Technology risks have also been reduced to acceptable levels for product development so that EAPs are commercially and technically becoming of increasing interest.

The improved performance and particular advantages of EAP materials give rise to applicability to new applications. In general terms, an EAP device can be advantageously employed in any application in which a small amount of movement of a component or feature is desired, based on electronic actuation. Similarly, the technology can be used for sensing small movements.

The use of EAPs enables functions which were not possible before, and offers significant advantages in comparison with other common sensor/actuator solutions, due to the combination of a relatively large deformation and force in a small volume or thin form factor. EAPs also give noiseless operation, accurate electronic control, fast response, and a large range of possible actuation frequencies, such as -1 MHz, most typically below 20 kHz.

Devices using electroactive polymers can be subdivided into field-driven and ionic-driven materials.

Examples of field-driven EAPs include Piezoelectric polymers, Electrostrictive polymers (such as PVDF based relaxor polymers) and Dielectric Elastomers. Other examples include Electrostrictive Graft polymers, Electrostrictive paper, Electrets, Electroviscoelastic Elastomers and Liquid Crystal Elastomers.

Examples of ionic-driven EAPs are conjugated/conducting polymers, Ionic Polymer Metal Composites (IPMC) and carbon nanotubes (CNTs). Other examples include ionic polymer gels.

Field-driven EAPs are actuated by an electric field through direct electromechanical coupling. They usually require high fields (volts per meter) but low currents. Polymer layers are usually thin to keep the driving voltage as low as possible. Ionic EAPs are activated by an electrically induced transport of ions and/or solvent. They usually require low voltages but high currents. They require a liquid/gel electrolyte medium (although some material systems can also operate using solid electrolytes). Both classes of EAP have multiple family members, each having their own advantages and disadvantages.

A first notable subclass of field driven EAPs are Piezoelectric and Electrostrictive polymers. While the electromechanical performance of traditional piezoelectric polymers is limited, a breakthrough in improving this performance has led to PVDF relaxor polymers, which show spontaneous electric polarization (field driven alignment). These materials can be pre-strained for improved performance in the strained direction (pre-strain leads to better molecular alignment). Normally, metal electrodes are used since strains usually are in the moderate regime (1-5%). Other types of electrodes (such as conducting polymers, carbon black based oils, gels or elastomers, etc.) can also be used. The electrodes can be continuous, or segmented.

Another subclass of interest of field driven EAPs is that of Dielectric Elastomers. A thin film of this material may be sandwiched between compliant electrodes, forming a parallel plate capacitor. In the case of dielectric elastomers, the Maxwell stress induced by the applied electric field results in a stress on the film, causing it to contract in thickness and expand in area. Strain performance is typically enlarged by pre-straining the elastomer (requiring a frame to hold the pre-strain). Strains can be considerable (10-300%). This also constrains the type of electrodes that can be used: for low and moderate strains, metal electrodes and conducting polymer electrodes can be considered, for the high-strain regime, carbon black based oils, gels or elastomers are typically used. The electrodes can be continuous, or segmented.

A first notable subclass of ionic EAPs is Ionic Polymer Metal Composites (IPMCs). IPMCs consist of a solvent swollen ion-exchange polymer membrane laminated between two thin metal or carbon based electrodes and requires the use of an electrolyte. Typical electrode materials are Pt, Gd, CNTs, CPs, Pd. Typical electrolytes are Li+ and Na+ water-based solutions. When a field is applied, cations typically travel to the cathode side together with water. This leads to reorganization of hydrophilic clusters and to polymer expansion. Strain in the cathode area leads to stress in rest of the polymer matrix resulting in bending towards the anode. Reversing the applied voltage inverts bending. Well known polymer membranes are Nafion® and Flemion®.

Another notable subclass of Ionic polymers is conjugated/conducting polymers. A conjugated polymer actuator typically consists of an electrolyte sandwiched by two layers of the conjugated polymer. The electrolyte is used to change oxidation state. When a potential is applied to the polymer through the electrolyte, electrons are added to or removed from the polymer, driving oxidation and reduction. Reduction results in contraction, oxidation in expansion.

In some cases, thin film electrodes are added when the polymer itself lacks sufficient conductivity (dimension-wise). The electrolyte can be a liquid, a gel or a solid material (i.e. complex of high molecular weight polymers and metal salts). Most common conjugated polymers are polypyrolle (PPy), Polyaniline (PANi) and polythiophene (PTh).

An actuator may also be formed of carbon nanotubes (CNTs), suspended in an electrolyte. The electrolyte forms a double layer with the nanotubes, allowing injection of charges. This double-layer charge injection is considered as the primary mechanism in CNT actuators. The CNT acts as an electrode capacitor with charge injected into the CNT, which is then balanced by an electrical double-layer formed by movement of electrolytes to the CNT surface. Changing the charge on the carbon atoms results in changes of C—C bond length. As a result, expansion and contraction of single CNT can be observed.

Figure 2:
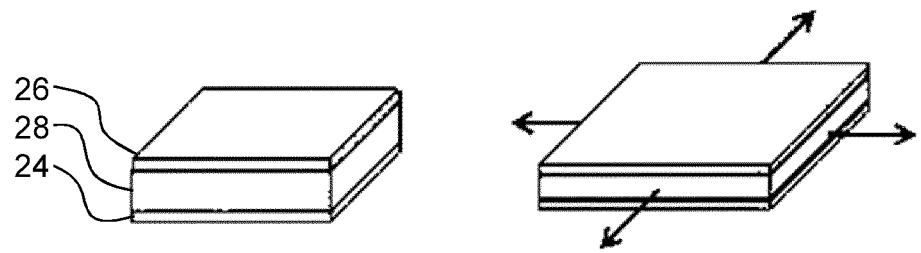
FIG. 2 shows a known electroactive polymer device which is not clamped.
Figure 3:
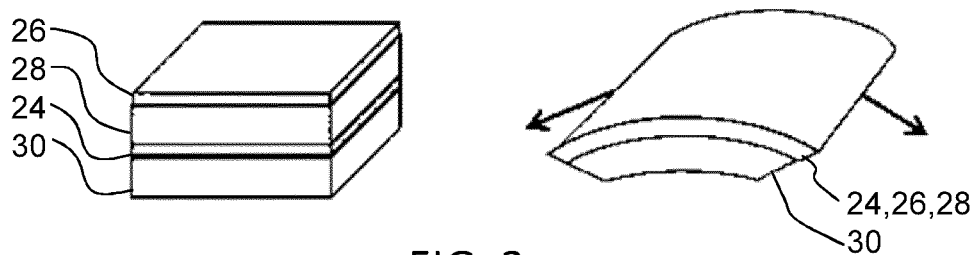
FIG. 3 shows a known electroactive polymer device which is constrained by a backing layer.

FIGS. 2 and 3 show two possible operating modes for an EAP device.

The device comprises an electroactive polymer layer 28 sandwiched between electrodes 24, 26 on opposite sides of the electroactive polymer layer 28.

FIG. 2 shows a device which is not clamped. A voltage is used to cause the electroactive polymer layer to expand in all directions as shown.

FIG. 3 shows a device which is designed so that the expansion arises only in one direction. The device is supported by a carrier layer 30. A voltage is used to cause the electroactive polymer layer to curve or bow.

Together, the electrodes, electroactive polymer layer, and carrier may be considered to constitute the overall electroactive polymer structure.

The nature of this movement for example arises from the interaction between the active layer which expands when actuated, and the passive carrier layer. To obtain the asymmetric curving around an axis as shown, molecular orientation (film stretching) may for example be applied, forcing the movement in one direction.

The expansion in one direction may result from the asymmetry in the EAP polymer, or it may result from asymmetry in the properties of the carrier layer, or a combination of both.

An electroactive polymer structure as described above may be used both for actuation and for sensing. It hence may be used to provide both actuating elements 14 in examples of the present invention, and sensing elements 16.

The most prominent sensing mechanisms are based on force measurements and strain detection. Dielectric elastomers, for example, can be easily stretched by an external force. By putting a low voltage on the sensor, the strain can be measured as a function of voltage (the voltage is a function of the area).

Another way of sensing with field driven systems is measuring the capacitance-change directly or measuring changes in electrode resistance as a function of strain.

Piezoelectric and electrostrictive polymer sensors can generate an electric charge in response to applied mechanical stress (given that the amount of crystallinity is high enough to generate a detectable charge). Conjugated polymers can make use of the piezo-ionic effect (mechanical stress leads to exertion of ions). CNTs experience a change of charge on the CNT surface when exposed to stress, which can be measured. It has also been shown that the resistance of CNTs change when in contact with gaseous molecules (e.g. $O_2$, $NO_2$), making CNTs usable as gas detectors.

Given that EAPs are able to operate either in an actuating mode or in a sensing mode, use of these materials carries the further significant advantage of allowing adaptability of surface interaction elements between operating either as an actuator or as a sensor. According to one or more examples, the controller may be adapted to switch an operation mode of one of more EAP-based surface interaction elements between actuation and sensing.

As noted above, this allows the configuration of the surface interaction elements to be adapted and altered to enable a broader selection and variety of different elasticity measurements to be obtained. By selectively switching different combinations of elements between actuation and sensing functionalities, different stretches of the receiving surface extending in different directions and corresponding to different distances or lengths for example can be analysed.

Additionally, this flexibility may allow for multiple different measures of elasticity to be gathered for a single given linear stretch of a receiving surface. Different elasticity measures may require different configurations of combinations of actuators and sensors to achieve. Where the operation of surface interaction elements is alterable, a multiplicity of these different measurements may in examples be performed over the same given area or section of the receiving surface.

An EAP-based actuating or sensing element may be formed of an EAP stack comprising a plurality of electroactive polymer electrode components, covered by a flexible insulator. When operating in actuation mode, the degree of deformation of the receiving surface may be controlled by controlling the actuation voltage applied to the actuating element.

Although EAPs are described as an advantageous example of a material for providing actuators and/or sensors, the invention is not limited to the use of EAPs to provide either the actuating elements or the sensing elements. Other alternative example materials for the actuating elements include other electroactive or electrically controllable materials such as for example liquid crystal polymer networks, liquid crystal elastomers, electrorheological elastomers, shape memory materials (e.g. heat activated shape memory materials), piezoceramics or magnetically controllable materials such as magnetostrictive materials.

Furthermore, other kinds of actuator not including electroactive or electrically controllable materials may be considered including for example actuators incorporating miniature actuator technologies based on inflatables, or MEMS actuation devices.

Likewise, the sensing elements may be provided by other force and/or pressure sensitive devices including, but not limited to, strain gauges, piezoelectric sensors (e.g. ceramics or PVDF-foils) and capacitive sensors.

In operation, measures of receiving surface elasticity may be obtained using surface interaction elements according to a number of different methods and modes. A selection of these different possible modes will now be described in detail. It is noted that any given embodiment of a surface analysis device may be adapted to implement one or any combination of these modes. Depending upon the size of the arrangement of surface interaction elements, multiple different modes may be implemented simultaneously, or may be implemented separately, by the controller.

Figure 4:
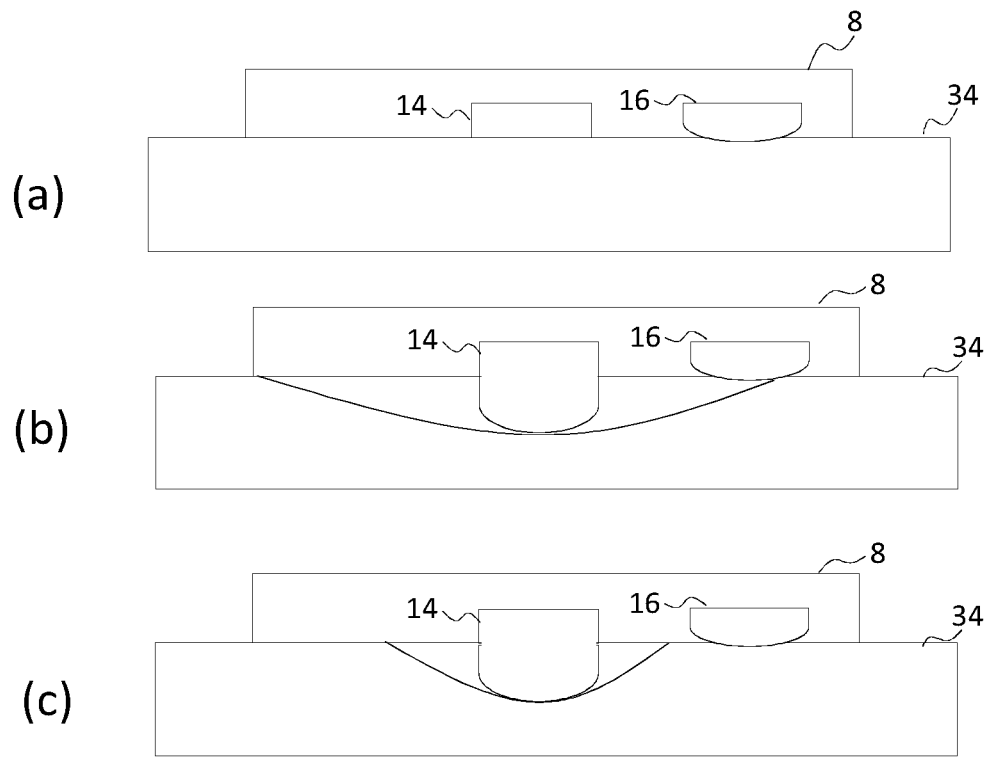
FIG. 4 schematically illustrates a first example elasticity measurement mode implementable in accordance with embodiments of the invention.

FIG. 4 illustrates a first example mode or method for obtaining a measure of an elasticity of a receiving surface. The figure shows a cross-sectional view of an example device being applied to a receiving surface 34. For the purposes of the present example, it will be assumed that the receiving surface is skin, although the example mode may also be applied to other receiving surfaces. A carrier 8 is shown supporting a single actuator 14 and single pressure sensor 16 against the surface of the skin 34. For the purposes of clarity, these two elements are shown only. However, it should be understood that embodiments of the device in real cases will comprise more than just two elements, and the present mode may be implementable using any pair of a larger given arrangement of elements.

FIG. 4*a* shows the arrangement in a first, inactive state, in which the actuating element 14 is idle. As shown in FIG. 4*b*, upon application of a control voltage by the controller (not shown in FIG. 4), the actuator deforms to expand in a direction extending downward toward the receiving surface.

This deformation has the effect of applying a force downwards onto the receiving surface 34, and thereby inducing an out-of-plane deformation (or indentation) in the surface of the skin 34.

In non-limiting examples, the actuating element may be an EAP-based actuator comprising one or more layers of EAP material, and adapted to deform in response to application of an electrical stimulus (as described above).

The sensing element 16 is adapted to measure a pressure applied to it by the receiving surface. This too may be formed by one or more EAP components, and utilised to measure a pressure in accordance with the methods described above. Alternatively, the sensing element may be a different kind of pressure and/or force sensor, such as a stress gauge, a piezoelectric sensor (e.g. ceramics or PVDF-foils) or a capacitive sensor.

FIG. 4b shows an example in which the skin layer (receiving surface) 34 is relatively stiff (or firm or inelastic). FIG. 4c by contrast shows an example in which the receiving surface is relatively less stiff (or firm, or more elastic). In the case that the receiving surface is relatively stiffer, the relative diameter of the induced indentation in the receiving surface 34 is greater. In the case that the receiving surface is less stiff, the relative diameter of the induced deformation is smaller.

It is noted that the term 'stiff' in the above description is to be interpreted broadly and may refer to skin which is firmer or less elastic, or may alternatively refer to one or more other physical properties giving rise to the illustrated behaviour. These properties may relate to the viscous behaviour of the skin for example or tension or slack in an upper skin surface layer.

The term 'stiff' or 'elastic' or 'elasticity' may refer to an 'effective elasticity', in which multiple physical properties and factors are taken into account. It may not refer directly to any particular classical measure of elasticity (such as elastic modulus) but may be a more general or broad concept intended to cover a wider set of properties and factors which can influence the deformation response of a typical region of skin.

This complex combination of various physical factors gives rise to the above-described result: that application of a locally focussed force to a point on skin exhibiting greater 'effective elasticity' or reduced 'stiffness' results in an indentation having smaller relative diameter.

As a result of the differing skin properties in each of FIGS. 4a and 4b, the pressure or force sensing element 16, located laterally displaced from the actuator 14, experiences a change in its measured pressure which is different in each of the two cases. In the case of the stiffer skin (FIG. 4b), in which the diameter of the induced indentation is greater, a greater area of skin 34 is pulled away from the base of the sensor, and hence the overall pressure applied to the sensor by the receiving layer is reduced. In the case of less stiff skin (FIG. 4c), in which the size of the induced indentation is smaller, less skin, or even no skin at all, is pulled away from the sensor, and hence any sensed reduction in pressure will be smaller.

By monitoring the pressure readings of the sensor 16 before and/or after deformation of the skin 34 therefore, an indication of the degree of skin elasticity may be achieved. In particular, this mode of measurement enables a measure of skin indentation resistance to be obtained (out-out-plane skin elasticity).

In particular examples, the pressure output of the sensor may be monitored both before and after activation of the actuator, and a change in pressure values determined. In other examples, the raw pressure values following activation alone may be captured.

In either case the captured or determined values may, in examples, further be compared or evaluated against some standard set of reference values, in order thereby to achieve some quantitative measure of the degree of elasticity. The values may also be input as variables into a physical model, the model enabling a quantitative measure of elasticity to be determined.

In either case, this further processing may, according to one or more examples, be performed by the controller itself or by a further analysis unit included in the device. Alternatively, the device may be adapted to output only the raw values themselves, with any analysis performed subsequently by an external system or by a human operator.

Where an EAP based actuator is used, it is possible to induce not only static deformations of the actuator, but also time-varying deformations, wherein the extent of actuator expansion varies as a function of time. A static deformation is achieved by application of a DC control signal to the actuator. An oscillating deformation may by contrast be achieved by applying an AC signal to the actuator.

Inducing a time-varying deformation in the actuator 14 causes the depth of the induced indentation to change (for example cyclically) over time. This may enable further dynamic measures of elasticity to be obtained. For example, a time varying deformation may induce travelling waves in the receiving surface 34. The velocity at which the waves travel through the skin may provide an indication of the elasticity of the skin.

Figure 5:
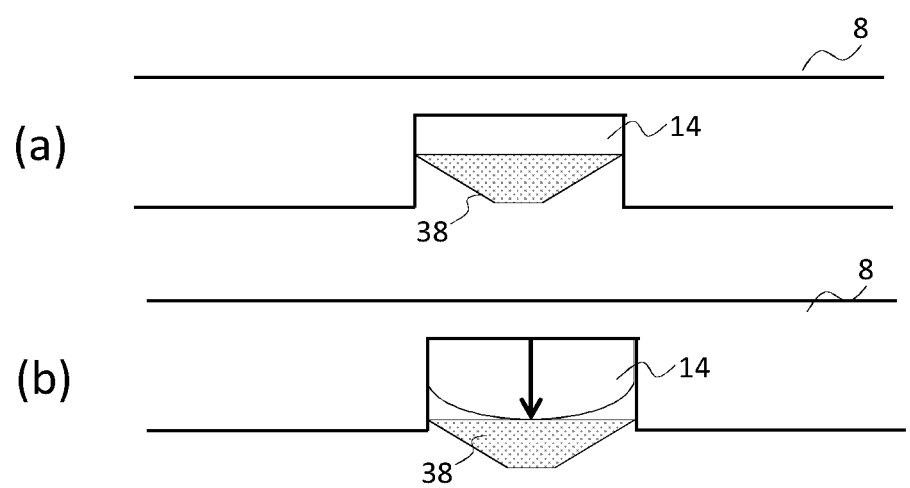
FIG. 5 schematically illustrates an adaptor for reducing an application area of a force induced by an example actuator.

According to one or more examples, the actuating element 14 may be provided with an adaptor for changing the area over which a force is applied to the receiving surface 34 by the actuating element. An example is shown in FIG. 5, which illustrates an adapter 38 designed to reduce the total area over which the deformation force of the actuator 14 is applied to the receiving surface. This consequently increases the pressure which is applied to the surface. FIGS. 5a and 5b shows the arrangement in idle and actuated states respectively.

In further examples, a different adapter may be provided, for example an adapter designed to increase the area over which a force is applied (and therefore reduce the magnitude of an applied pressure).

The example of FIG. 4 illustrates a method of determining indentation resistance of a receiving surface based upon application of an out-of-plane deformation in the surface, and upon measuring an out-of-plane pressure and/or force exerted by the receiving surface.

According to further examples, one or more measures of in-plane elasticity may also be achieved. In a simple first example, this may be obtained using a variant of the example arrangement of FIG. 4, wherein two actuators 14 are provided, one positioned either side of the sensor and which are operable to expand laterally (in a direction substantially parallel with the receiving surface). The sensor 16 is provided operable to measure a lateral force applied across its lower active surface.

By stimulating the two actuators to laterally deform simultaneously, a stretching of the region of skin lying between them is achieved (i.e. an in-plane deformation of the skin is effected). The sensor positioned between the two actuators is controlled to monitor the lateral (in-plane) forces exerted across its lower surface by the receiving surface. Depending upon the elasticity of the skin, a different magnitude of force will be measured by the sensor for a given lateral deformation of the actuators. In particular, the measured force after deformation will be greater for skin which is relatively stiffer, and will be lower for skin which is relatively looser or more elastic.

Again, the controller may be configured to calculate a change in the measured force (before and after actuation), or simply to capture the raw force values. These calculated or raw values may again be compared with some standard set of reference values in order to obtain a quantitative measure of skin (or other surface) in-plane elasticity. The values may alternatively be processed using a physical model to thereby obtain a quantitative elasticity measure.

According to a further example variation, the example mode of FIG. 4 may simply be extended to include two actuating elements 16 (positioned either side of the sensing element 18) both operable to induce out-of-plane deformations (indentations).

The two actuators may be stimulated by the controller to induce simultaneous indentations in the surface on either side of the sensing element. In this case, a combination of both indentation and stretching is achieved. The sensor may measure a convolution of these two effects.

The sensor in this case may be operable to measure a lateral force applied across its lower active surface, or may be operable to measure an out-of-plane (i.e. perpendicular to the receiving surface) force applied to its lower active surface. In either case, the sensor signal output may be affected by both indentation and stretching effects, and the obtained pressure/force measurements may therefore provide a measure which reflects both of these physical effects.

Figure 6:
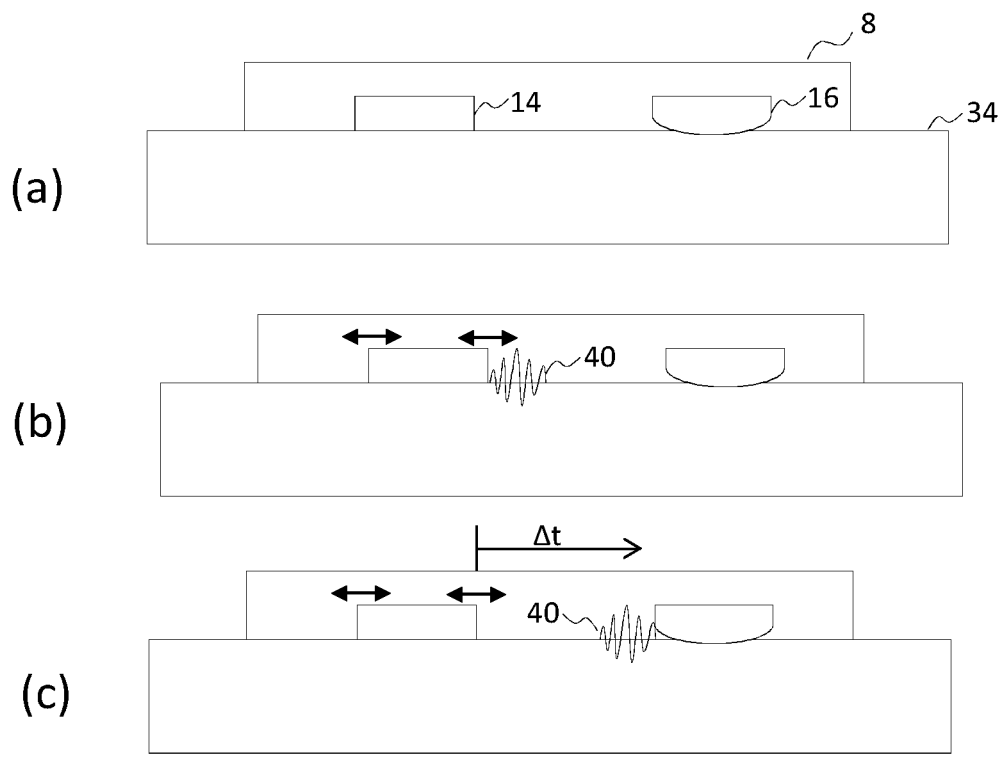
FIG. 6 schematically illustrates a second example elasticity measurement mode implementable in embodiments of the invention.

FIG. 6 shows a further example operating and measurement mode by means of which a further alternative measure of surface elasticity can be obtained. In this case, the provided carrier 8 of the device holds an arrangement which includes an actuating element 14 operable to produce in-plane deformations, and a sensing element 16 operable to sense in-plane or out-of-plane pressures and/or forces. Again, although only two elements are shown for the purposes of this example, true embodiments of the invention include arrangements comprising more than two elements. Multiple pairs of such arrangements may be controlled in accordance with the present operating mode to achieve multiple elasticity measurements.

As shown in FIG. 6b, the actuating element 14 is stimulated with a time-varying control voltage, causing it to deform laterally in a time-varying fashion, thereby inducing a time-varying in-plane deformation in the receiving surface 34. This manifests in the generation of a surface (acoustic) Lamb wave 40 which propagates across the surface 34.

As shown in FIG. 6c, this wave 40 is detected by the sensing element 16 as a pressure wave after a time delay Δt. Based on the time delay, a velocity of the wave can be calculated.

There is a positive correlation between the speed of elastic shear wave propagation and the stiffness of the material through which it is travelling. As a consequence, the value of the wave velocity provides an indication of the receiving surface elasticity. In particular, in the case that the method is applied to skin, the velocity of this surface acoustic (Lamb) wave may provide an indication of the viscoelasticity of a user's skin.

This mode of measurement (or the mode illustrated in FIG. 4) may be expanded in further examples by inclusion of additional sensing elements 16 positioned in proximity to the actuating element 14. Each sensing element may in examples be positioned adjacent to the actuator (with no other elements in-between), for example forming an annular arrangement which surrounds a central sensor.

Such a configuration enables multiple elasticity measures (either indentation or viscoelasticity measures) to be obtained simultaneously, since a single deformation pattern generated by the central actuator can be sensed or monitored by each of the surrounding sensing elements at the same time Such a configuration allows for faster data recording for example, and more efficient power consumption.

Figure 7:
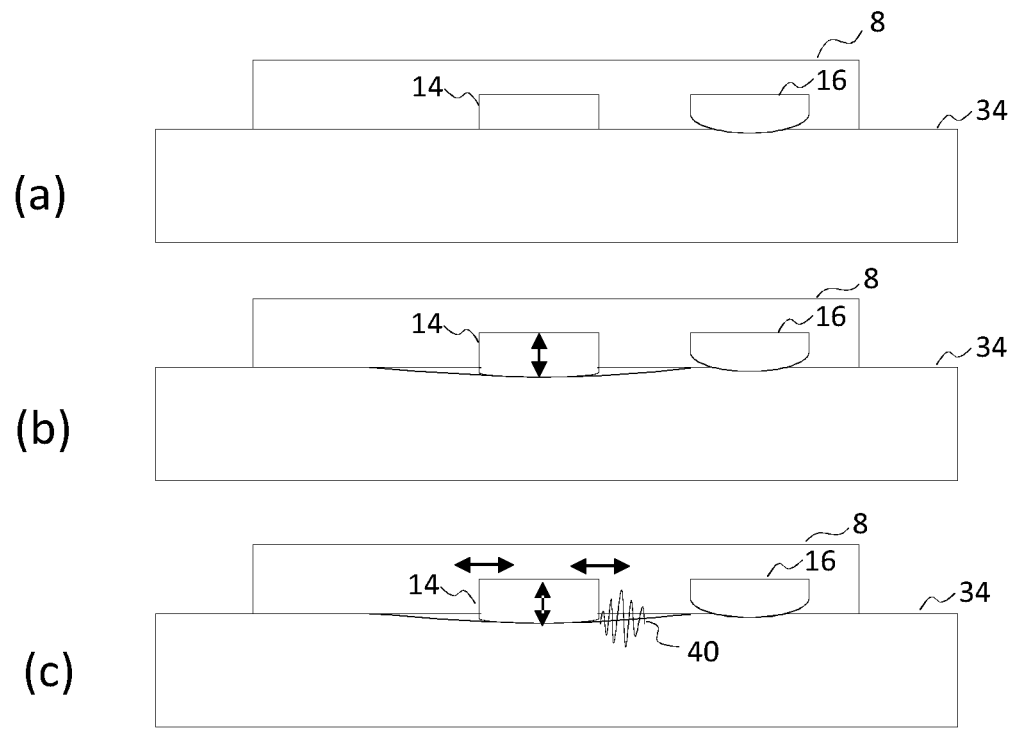
FIG. 7 schematically illustrates a third example elasticity measurement mode implementable in accordance with embodiments of the invention.

FIG. 7 shows a variation on the example operating mode of FIG. 6, in which the actuation element 14 is operable to expand both laterally and perpendicularly (i.e. both parallel and perpendicular to the receiving surface 34). As shown in FIG. 7b, the actuator is first controlled to deform statically in a direction perpendicular (normal) to the receiving surface to induce a static (non-time varying) out-of-plane deformation (indentation) in the receiving surface.

As shown in FIG. 7c, the actuator 14 is then simultaneously controlled to deform laterally in a time-varying fashion. The time-varying lateral expansion stimulates a resultant surface acoustic (Lamb) wave 40 which propagates along the (already indented) receiving surface 34 in the direction of a laterally displaced sensing element 16. The sensing element is configured to detect arrival of the wave, as in the example of FIG. 6. Based on a measured time of arrival, the velocity of the wave can again be determined.

The static out-of plane deformation serves to adjust a static (baseline) pressure of the actuator 14 on the receiving surface 34. This may enable adjustment of the coupling of the actuator to the receiving surface, or may enable multiple measurements of wave 40 velocity to be attained, corresponding to different static pressures. The static pressure in the latter case provides an additional degree of freedom in the system, which may allow a richer and more detailed analysis of surface elasticity to be achieved.

The simultaneous stimulation of both static perpendicular and time-varying lateral expansion of the actuator may be achieved in examples by applying superposed DC and AC signals to an EAP element. A high-magnitude DC signal generates the static expansion in a direction normal with the receiving surface and a low-amplitude AC signal generates the time-varying expansion parallel with the receiving surface. This may work best with use of a dielectric elastomer. PVDF-based relaxor polymers may also be used, although achievable displacement is smaller.

Figure 8:
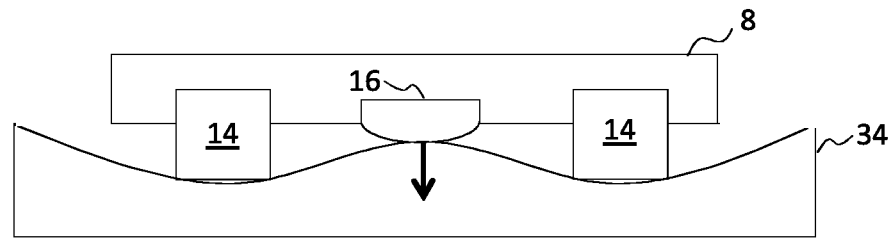
FIG. 8 schematically illustrates a skin adhesion or friction measurement means implementable in embodiments of the invention.

In accordance with a further example operating mode, a measure of skin adhesion and friction can be obtained. This is achieved by measuring a so-called peel-off force of a sample of skin upon indentation and displacement of the skin. FIG. 8 schematically depicts an example configuration for achieving this measurement. The arrangement includes two actuators 14 operable to generate out-of-plane deformations in the skin surface 34, the actuators positioned surrounding a central sensing element 16.

The sensing element 16 in this case must be operable to measure both positive and negative forces/pressures; it must be operable to measure a force or pressure exerted by the receiving surface in a direction inwards towards the surface (i.e. a 'pulling force' away from a lower surface of the sensing element itself) as well as a force in a direction upwards towards its own lower surface.

As shown in FIG. 8, upon activation of both actuators 14, the resultant deformation in the skin surface 34 applies a downward force which acts to pull the skin away from the surface of the sensing element 16. As the skin is pulled away, it pulls down on the sensor 16 with a magnitude which is dependent upon the skin adhesion. The peak value of this downward pulling force is known as the 'peel-off' force.

For improved sensitivity, the peel off force can be enhanced by using a relatively smooth and/or soft sensor surface which may amplify the skin adhesion properties. Skin adhesion and skin friction are correlated, and hence a measure of the adhesion (or 'stickiness') provides an indication of the friction.

Figure 9:
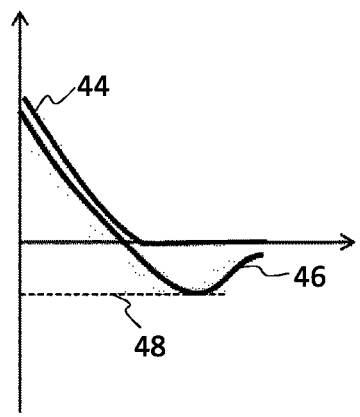
FIG. 9 shows example actuator voltage vs sensor output curves achieved using the skin adhesion or friction measurement method.

The peel-off force (and hence skin adhesion) can be determined from the actuator voltage—sensor output curve. Two examples of such curves are shown on the graph of FIG. 9, in which the x axis represents actuator 14 voltage and the y-axis represents force measured by the sensing element 16.

Curve 44 shows the output curve which is attained for skin having low adhesion and friction. Here, the measured force approximately linearly decreases to zero as the deformation of the actuators is increased, and then remains at zero for all further actuation voltages. This indicates that there is zero experienced peel-off force; skin adhesion is too low to cause any measurable sticking of the skin to the sensor 16.

Curve 46 shows the output curve which is attained for skin having high(er) adhesion and friction. Here, again, measured force decreases linearly to zero with increasing voltage, but then continues to decline into negative force measurements, reaching a minimum value indicated by dashed line 48. The dashed line 48 indicates the 'peel-off force': the force necessary for the skin to begin to separate from the sensor. Past the peel off force, the measured force increases approximately linearly again up to zero, indicating that the skin is slowly unpeeling itself.

By analysing obtained actuation voltage vs sensor output curves, the peel-off force for a given skin sample can be determined and a measure of skin adhesion and friction therefore obtained.

In variations, one actuator and one sensor only may be used to measure peel off force, provided that the two are placed sufficiently close together.

Figure 10:
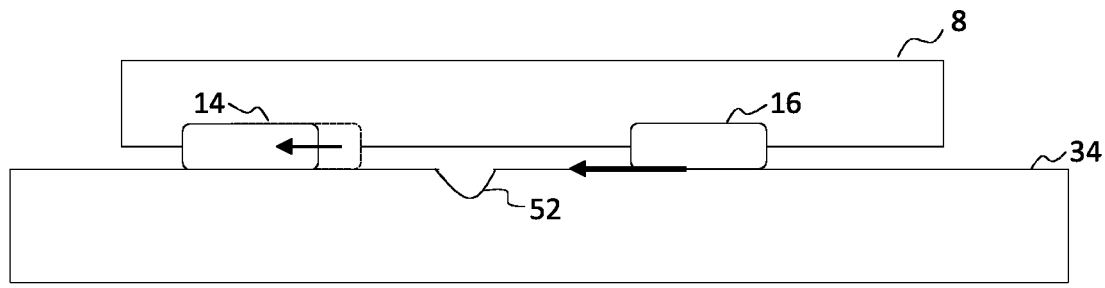
FIG. 10 schematically illustrates a wrinkle location and/or size measurement method implementable in embodiments of the invention.

According to a further example operating mode, measurement of a size and/or location of a skin wrinkle may be performed. This mode is illustrated in FIG. 10. An actuator 14 operable to deform laterally is utilised in combination with a sensor 16 operable to measure either in-plane or out-of-plane forces or pressures. It is assumed that a wrinkle 52 is located in-between the actuator and sensor. Upon activation of the actuator, a lateral in-place force is applied to the skin, pulling it in a direction indicated by the arrow.

Figure 11:
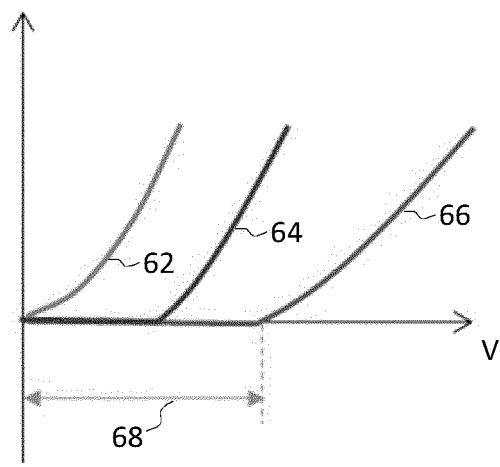
FIG. 11 shows example actuator voltage vs sensor output curves achieved using the wrinkle location and/or size measurement method.

Depending upon the size of the wrinkle 52 (and whether or not there is a wrinkle present at all), different actuation voltage vs sensor output curves are obtained. FIG. 11 shows a number of different example curves corresponding to different wrinkle scenarios, in which the x-axis represents actuator voltage, and the y-axis represents sensor output.

Where there is a wrinkle between the sensor 16 and actuator 14, the sensor initially registers zero output (or at least a very weak output), while the wrinkle 52 is being 'unfolded'. After the wrinkle has been fully unfolded, the sensor output rapidly increases due to the inherent skin elasticity. The actuator voltage (i.e. the displacement) necessary to fully unfold the wrinkle ('threshold voltage') provides an indication of the size of the wrinkle (width, depth, volume).

This is illustrated in FIG. 11, in which curves 64 and 66 represent output curves corresponding to a smaller and larger wrinkle 52 respectively. In each case, sensor output remains close to zero up to a given threshold voltage. Once this threshold is passed, the sensor output begins to increase.

The threshold voltage for the larger wrinkle trend-line 66 is illustrated on the graph by arrow 68. The smaller wrinkle has a smaller threshold voltage.

Curve 62 corresponds to the case in which no wrinkle is present. As shown, here the sensor output simply increases with increasing voltage, without any initial delay or pause.

By analysing the obtained actuation voltage vs sensor output curve, the presence and/or size of a wrinkle can be evaluated.

Figure 12:
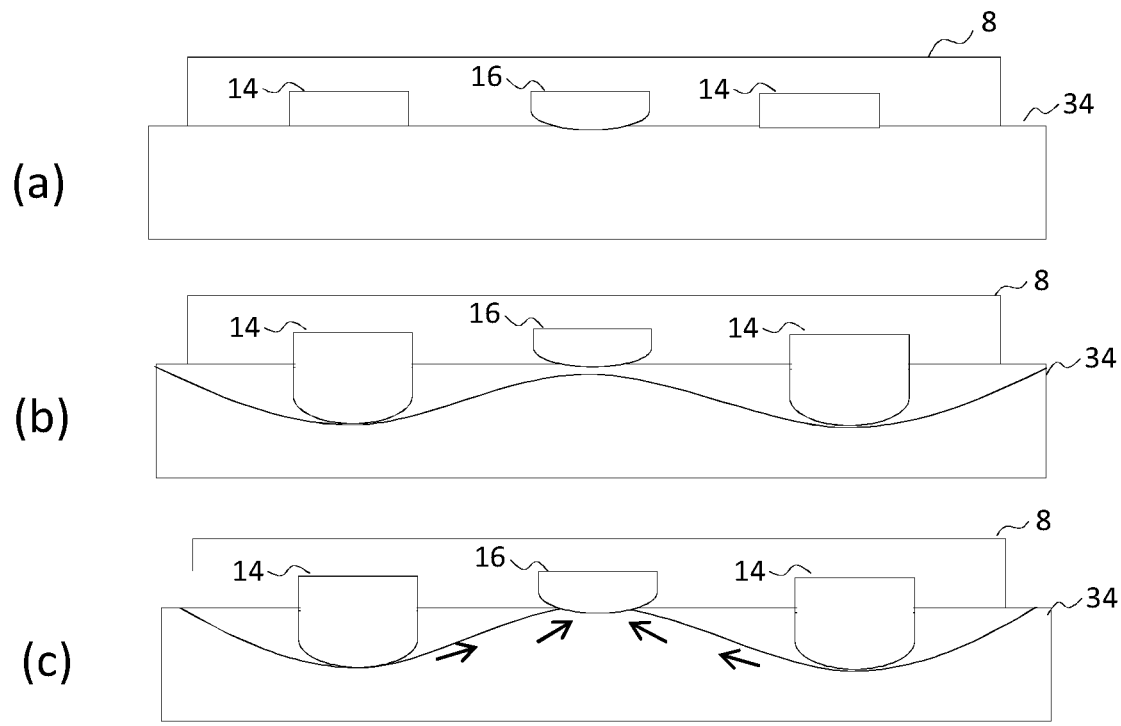
FIG. 12 schematically illustrates a fourth example elasticity measurement implementable in embodiments of the invention.

FIG. 12 illustrates a further example operating mode in accordance with embodiments of the invention. An arrangement is used which includes two actuating elements 14 operable to induce out-of-plane deformations in the receiving surface 34, and a sensing element 16 situated in-between the two actuators, operable to measure an out-of plane pressure and/or force exerted by the receiving surface in a direction upward toward the sensor.

This arrangement effectively represents an expansion of the example measuring mode illustrated with reference to FIG. 4, wherein two deforming actuators 14 are provided instead of one.

FIG. 12a shows an initial inactive state. FIG. 12b illustrates activation of both actuators 14 in the case of relatively stiffer skin. FIG. 12c illustrates activation of both actuators in the case of relatively less stiff skin.

In the case of stiffer skin (FIG. 12b), activation of both actuators 14 causes a large pressure drop at the sensor 16. Indeed, FIG. 12b shows an extreme case in which the skin is fully separated from the sensor, resulting therefore in 100% pressure drop. This effectively represents the same result as is expected to be achieved in the example mode of FIG. 4, but with a greater overall induced pressure drop.

In the case of less stiff skin (FIG. 12c), more interesting results may be obtained. In a first instance, lower-stiffness skin will result in a lower measured pressure drop at the sensor 16 (as was the case for the FIG. 4 example). However, in some cases, there may in fact be measured a net pressure rise, occurring as a result of an induced doming arising from the application of symmetric pressure on both sides.

More flexible skin allows the downward pressure applied by the actuators 14 on either side of the sensor 16 to be re-directed at least partially inward and upward toward the sensor. This pressure may in some cases manifest itself in an upward applied pressure onto the lower sensing surface of the sensor (as shown in FIG. 12c). The degree of doming will depend upon the stiffness of the skin. Hence, this extended arrangement incorporating two indenting actuators allows for additional information about the skin stiffness to be obtained in comparison with the configuration and operating mode of FIG. 4.

Figure 13:
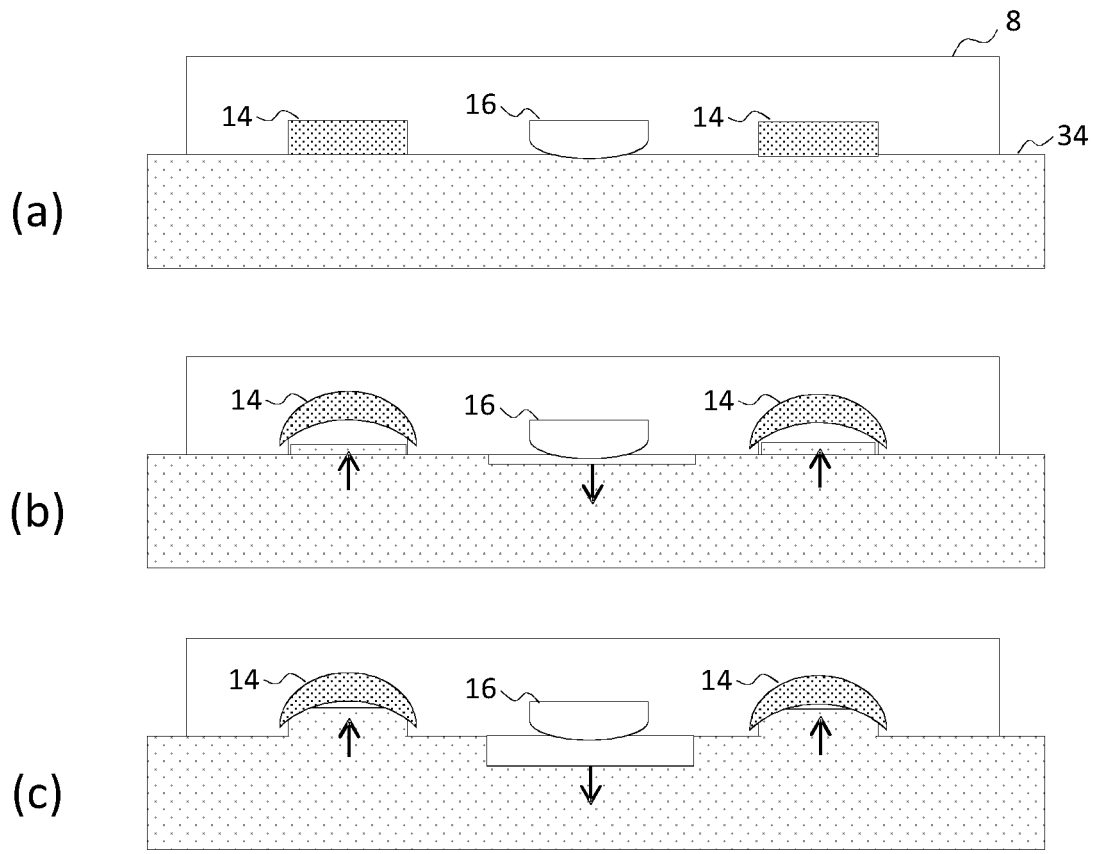
FIG. 13 schematically illustrates a fifth example elasticity measurement mode implementable in embodiments of the invention.

FIG. 13 shows a further example operating mode for obtaining a measure of an elasticity of a receiving surface. This example effectively represents a 'reverse' of the previous mode illustrated with reference to FIG. 12. Here, two actuating elements 14 are utilised, positioned on either side of a central sensing element 16. The sensing element is adapted to measure an out-of-plane pressure and/or force exerted by the receiving surface 34 in a direction away from the receiving surface.

Each of the actuators 14 is operable to deform in a direction away from the receiving surface 34 as illustrated in FIGS. 13b and 13c. Since the surrounding carrier 8 matrix is applied firmly to the receiving surface, this deformation produces an effective vacuum effect within the gap left vacant by the actuator deformation. This vacuum effect causes the skin (or other receiving surface) below to be partially pulled upward to occupy a part of said gap created by the deformation. This effectively induces an undulation in the skin, which causes the region of the skin lying symmetrically between the two actuators to drop downwards. Where this region is aligned with the sensor element 16, this dropping will be detected as a fall in applied upward force or pressure.

The magnitude of the measured pressure drop will depend upon the stiffness of the skin 34. FIG. 13*b* shows the case for a sample of stiff skin. Here, the fall in the central region of skin is small, and hence the measurement pressure drop is small. FIG. 13*c* shows the case for less stiff skin. Here the pressure drop is much greater. By analysing the output values of the sensor, a measure of the skin elasticity or stiffness may be obtained.

In variant examples, the sensor 16 may be a displacement sensor instead of a pressure or force sensor.

Any of the above-described modes and configurations may be advantageously incorporated or implemented in any example embodiment of the invention. Multiple different modes may be implemented simultaneously in certain cases, or the controller may be adapted to switch between different modes to achieve different forms of measurement.

The first example device embodiment of FIG. 1 described in previous passages above, illustrates a simplest case of the present invention, in which an arrangement of only three surface interaction elements is provided. However, the concept of the invention allows advantageous expansion to cover arrangements including any number of different elements, arranged to follow any desired pattern or configuration. More complex patterns may allow for a richer or more detailed set of measurement data to be obtained.

Figure 14:
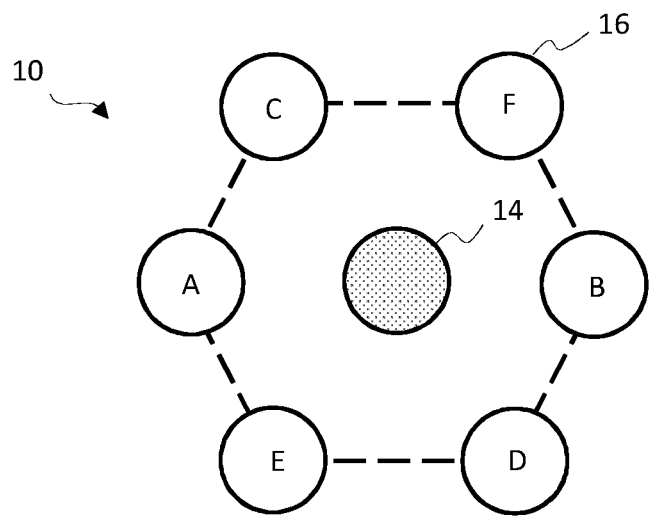
FIG. 14 schematically illustrates n example arrangement of surface interaction elements in accordance with embodiments of the invention.

FIG. 14 shows for instance a first alternative example arrangement 10 of surface interaction elements which may be incorporated within example embodiments. The arrangement comprises a hexagonal annular arrangement of six sensing elements 16 surrounding a central actuating element 14. The arrangement allows for multiple elasticity measures to be obtained corresponding to different directions. As discussed above, multi-directional information enables anisotropy information to be obtained.

For example, one elasticity measure may be obtained for each stretch of skin lying between each sensor 16 and the central actuator. This may be achieved by activating the central sensor to induce a deformation (in-plane or out of plane, in accordance with any of the modes described above), and controlling each of the surrounding to sensors to measure a resultant pressure. Sensor readings may in this case be taken concurrently, thereby achieving six measures of elasticity, corresponding to six different directions, at the same time.

In a variation on the arrangement of FIG. 14, an annular array of multiple actuators may instead be provided surrounding a single sensing element. This arrangement also allows elasticity measures to be obtained for each of the skin sections lying between each of the actuators and the central sensor.

However, this variant arrangement also allows for implementation of certain other of the modes of elasticity measurement described above. For example, each pair A-B, C-D, E-F of actuators may be activated in combination with the central sensor to achieve a measurement in accordance with the mode described with reference to FIG. 12 above.

Where an appropriate sensor is provided (one operable to measure both positive and negative pressures), a measuring mode in accordance with the example of FIG. 8 may additionally be implemented.

Where appropriate actuators are provided (i.e. ones operable to deform away from the receiving surface), the measurement method of FIG. 13 may also be implemented. Multiple different varieties of actuator may be provided to enable implementation of a plurality of these different modes.

Although a hexagonal arrangement is illustrated by way of example, any configuration may equally be utilised, for example rectangular, pentagonal, or any other regular or irregular shape or configuration. A hexagonal arrangement confers the advantage of allowing multiple different directional measures to be obtained, while also providing good tessellation between neighbouring arrangements to thereby allow for expansion of the arrangement to an arbitrary size.

In further examples, the shape or size of each surface interaction element may be varied, or the pitch between neighbouring elements varied across the arrangement.

Figure 15:
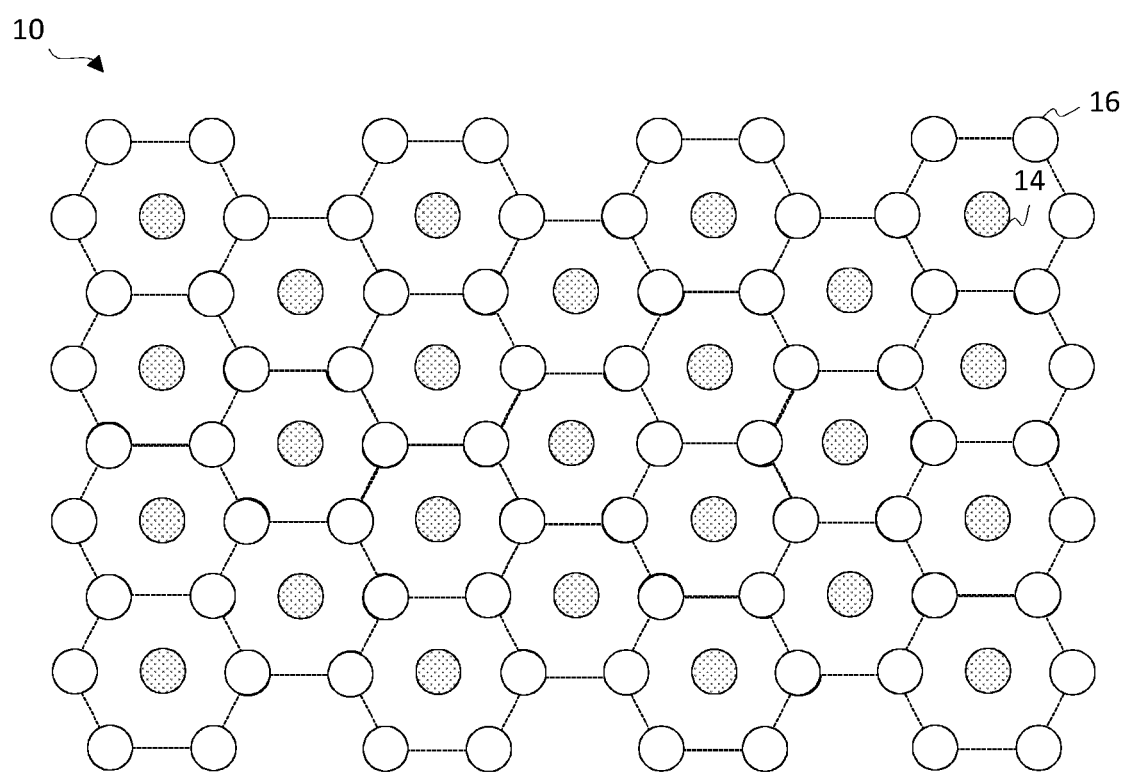
FIG. 15 schematically illustrates a second example arrangement of surface interaction elements in accordance with embodiments of the invention.

As noted above, the arrangement of sensors and actuators may be expanded to any arbitrary desired size. FIG. 15 shows an example arrangement of multiple tessellated hexagonal configurations of sensors 16 and actuators 14.

The arrangement effectively comprises a plurality of the arrangements of FIG. 14. Each pair of neighbouring hexagonal 'cells' or configurations share two of their six sensing elements between them. This sharing of elements leads to efficient utilisation of sensing resources, enabling large numbers of different elasticity measures to be obtained using a reduced total number of sensing parts.

The controller may control any arbitrary sensor-actuator pair in the arrangement 10 to provide a respective elasticity measurement. This enables large numbers of measures to be obtained, not only for different directions, but also across different distances and for different local locations.

Figure 16:
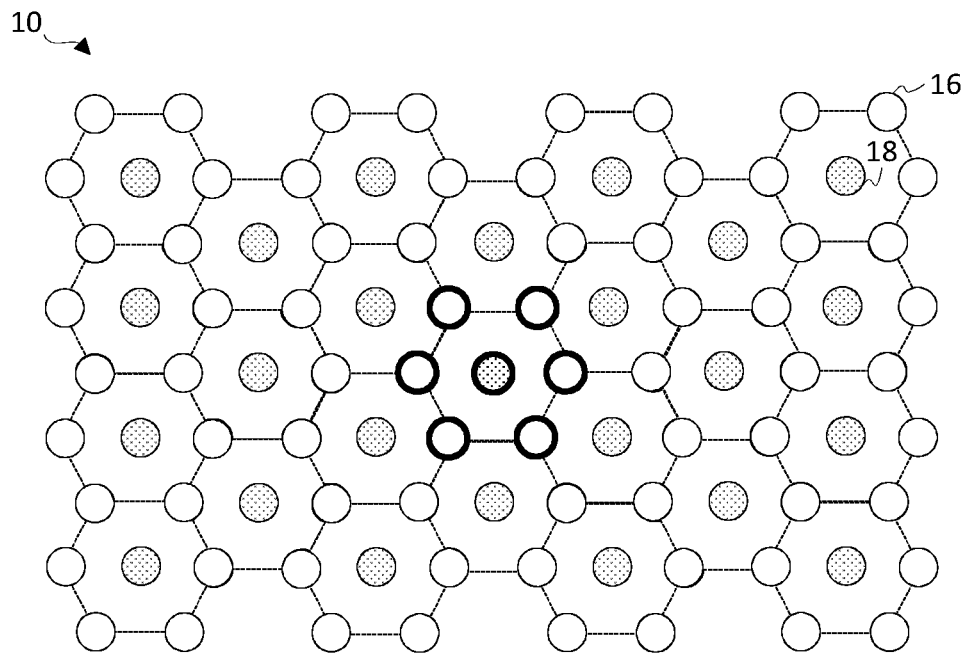
FIG. 16 illustrates an example operation mode for the second example arrangement of surface interaction elements.
Figure 17:
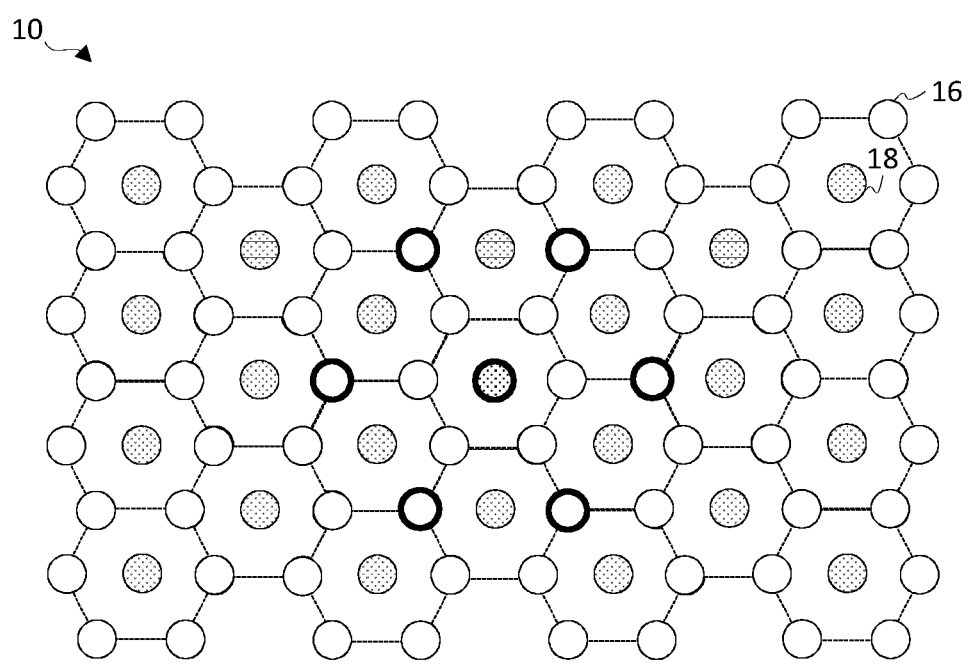
FIG. 17 illustrates a second example operation mode for the second example arrangement of surface interaction elements.

FIGS. 16 and 17 illustrate utilisation of different example selections of elements within the arrangement 10 of FIG. 15 to enable elasticity measures corresponding to different distances across a receiving surface. The bold outlined elements are elements being actively controlled by the controller.

As shown in FIG. 16, an initial set of measurements may be taken between a central actuator 14 and each of six immediately surrounding sensors 16. Once these measures are obtained, the six sensors located one 'layer' out from the first hexagonal ring may be utilised in combination with the central actuators to obtain a further six elasticity measures, corresponding to the same set of directions, but across a wider distance.

These represent just two example operation or activation modes, and clearly any arbitrary combination or pattern of elements may be activated to achieve different sets of measurements. Individual pairs of elements may be activated for instance, or rings or patterns of sensing elements following a non-hexagonal shape. Lines of multiple elements may be utilised for multiple measurement, or multiple lines utilised simultaneously or sequentially.

In accordance with any example arrangement, multiple different elasticity measures may in some examples be averaged or otherwise combined, to provide average or amalgamated elasticity measures for a given area. For instance multiple measures for different directions may be averaged, to provide a single measure of elasticity for a particular area or region.

As discussed briefly above, use of EAP-based sensing and actuating allows for bi-functional surface interaction elements to be provided, each element operable to function either as an actuator or as a sensor, as required. Use of such bi-directional elements allows for a far denser set of data to be obtained with a given arrangement of elements that would otherwise be possible. This is because bi-directional elements allow for arbitrary combinations of actuators and sensors to be realised.

Such bi-functionality may also be realised in alternative examples by adding separate dedicated sensing functionality to one or more actuators. This may be achieved by, for example, adding a pressure (or force or bending) sensor to the actuator. In one or more examples, such a sensor device or element may be attached underneath the actuator, on the receiving-surface-facing lower surface of the actuator. This would allow sensing to be performed where desired, but without necessarily interfering with actuation function. Such a sensor may consist in examples of a resistive, capacitive or piezoelectric flexible film element which may be bonded to the actuator using adhesive for instance or by direct printing onto the actuator.

Although bi-functional actuator is operable to achieve either sensing or actuation, the two would not be utilised simultaneously. The added functionality confers advantages only in that it allows arbitrary switching between the two different operation modes.

Figure 18:
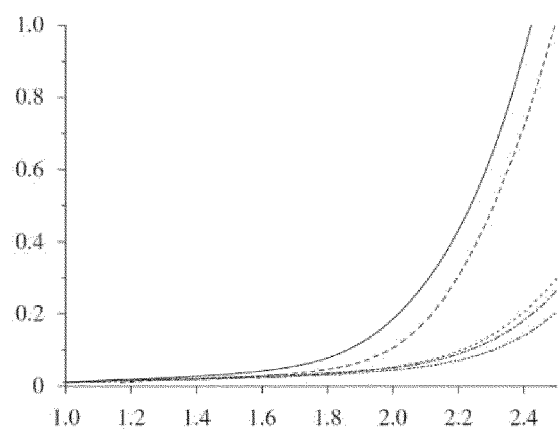
FIG. 18 shows different stress-strain curves for a sample of skin measured at different temperatures.

According to one or more example embodiments, temperature sensing capability may be advantageously incorporated into one or more of the surface interaction elements. Skin elasticity properties are highly dependent upon temperature. This is illustrated in FIG. 18 which shows 5 different example stress-strain curves for samples of skin, each corresponding to a different skin temperature. The x-axis represents stress (in MPa) and the y-axis represents strain. From uppermost to lowermost, the curves correspond to skin temperatures of 10° C., 15° C., 40° C., 50° C. and 60° C. respectively.

Incorporation of temperature sensing may enable elasticity measurements to be corrected for temperature, and hence more accurate and reliable results to obtained.

Temperature sensing may be directly achieved using EAP-based actuators, since these are capable of measuring temperature simultaneously with actuation. This may be achieved in examples by superposing a low-amplitude AC signal for determining temperature with a high magnitude DC signal for inducing actuation. An appropriate AC signal may cause an exhibited impedance across the EAP element to change depending upon the temperature at which actuation is performed (as well as the DC drive signal applied).

A calibration process may be performed in advance of operation, wherein an inductance across the EAP element is measured for each of an anticipated possible range of applied DC drive signals, at each of a desired range of different temperatures. A look-up table of corresponding exhibited impedances for applied DC signal at each different temperature may accordingly be generated. This look-up table may be used in operation of embodiments of the device to determine, based on a measured impedance and upon a known applied DC drive signal, an estimated temperature of the EAP element.

Further to this, it may be of advantage to obtain measures of skin elasticity at a range of different temperatures. The elastic behaviour of skin as a function of temperature provides a richer dataset than measurement at a single temperature alone.

To achieve this, in accordance with one or more example embodiments, a heater element may be incorporated with one or more of the actuators, for example affixed behind the actuator, which allows the actuator and the skin beneath it to be heated.

Temperature may be sensed in these examples again as outlined above, and a series of elasticity measurements may be performed at different temperatures in order to achieve analysis of elasticity as a function of temperature.

Alternatively, a heating element may be place in front of the actuator (on the skin-facing side). However, this may interfere with the actuation performance of the actuator in some cases, by preventing close contact between the actuator and the skin.

A heater/cooler element (such as a Peltier element) may be used in some examples for more accurate temperature control.

Additionally, temperature sensing functionality may be used to determine thermal properties of the skin. For instance, temperature sensing may enable the position of one or more anatomical features (such as arteries) to be identified. For the case of locating the position of an artery for example, the difference in heat conductivity of the skin may be determined. The heat conductivity will be higher in the vicinity of an artery close to the skin surface due to the transport of heat by the flowing blood. By tracking the decrease in temperature of each sensor after deactivating the heating element, regions with the highest thermal conductivity can be identified. This may indicate presence of an artery under the skin surface.

An artery or other anatomical feature may be a region of interest for performing elasticity measurements for example.

Use of multiple sensor outputs (as described in examples above) may enable more accurate results by allowing for noise to be eliminated through calculation of one or more differential sensor results. For example a differential sensor output may be calculated as follows:

$$|S_{tot}|=|(S_m+\text{noise})-(S_n+\text{noise})|=|S_m-S_n|$$

where $S_m$ and $S_n$ are sensor outputs corresponding to the same transmitted signal generated by the same actuator and sensed by each of sensor m and n respectively. $|S_{tot}|$ represents a differential sensor result in which noise has been cancelled out.

Applications for embodiments of the invention are wide and varied.

The invention is applicable generally in the field of surface analysis. A range of industries may benefit from the improved capacity offered by the invention to measure and analyze elasticity of lateral stretches of a receiving surface extending in multiple directions. The present invention enables anisotropy in the lateral elasticity of a surface to be measured and analyzed.

Example applications may include the testing of fabric elasticity, such as for clothing, carpets, seating, or other fabric furnishings such as curtains. The capacity to analyze elasticity with greater sophistication and detail may be useful for instance in assessment of probable lifetime of fabrics or materials used in such applications. For instance the device might be used to assess the surface elasticity across different linear regions of an area of fabric for a chair. This may enable assessment, based also on typical weight distribution of persons when sitting on a chair, of likely areas of most wear or strain in the material, and likely useable lifetime. The areas predicted to experience most strain might be strengthened or thickened by an amount dependent on the elasticity measurements obtained using embodiments of the invention.

Similarly, for application to materials for curtains, it may be useful for instance to assess the elasticity in different directions of the material, so as to determine in which orientation to cut the fabric for least gravity-induced stretching of the curtains. There are likewise applications for materials used in a wide range of industrial or commercial areas in which in-plane elasticity of the material when in use is an important factor.

It also known that analysis of elasticity of animal hides is a useful tool, and the added ability of the present invention to measure anisotropy in elasticity across different stretches of the hide may be a valuable additional functionality.

Further to the above examples, a wide range of applications exist relating in particular to skin analysis.

Example devices, especially when implemented as in a thin, flexible patch for instance, would be suitable in beauty therapy applications. Measurements of skin elasticity may be used to subsequently advise on treatment of the skin, especially effects of ageing on the elasticity of the skin. Other causes (besides aging) might be Cutis laxa, Erythema multiforme, sun damage and weight loss.

Also diseases can be related to changes in elasticity. The skin normally stretches and returns to its normal position if it is well hydrated and healthy. Hyper elastic skin stretches beyond the normal limit. Although this is not usually cause for concern, hyper elastic skin can be a symptom of many diseases and conditions. For instance Ehlers-Danlos syndrome, the Marfan syndrome, the Brittle bone disease and the Aarskog syndrome.

A further application may be to assess the elasticity of suspicious birthmarks or other skin defects as a means of differentiating them from non-malignant defects. The pitch of actuators and sensors in this case may be small to enable a plurality of these elements to cover a small skin defect.

Proposed embodiments could be used in applications where elastic materials have to be characterized.

Besides the uses outlined above, potential applications include:

Identifying positions of arteries for the purpose of PPG blood pressure/heart rate monitoring. Actuators positioned above the artery where blood pressure has to be measured may be activated;

Elasticity variation information across a region of facial skin may be advantageous used to adapt a shaver rotation of oscillation speed for a smoother shave (a mini EAP-Sensor array may be incorporated within a skin-contacting portion of a shaver for instance);

Elasticity information can be used to optimize topical dosing to the skin, for example of moisturizers or other creams;

Skin friction can be measured by moving an example device over the skin to characterize skin friction variations at different locations. This information can be used to optimize beauty treatments for instance.

Materials suitable for the EAP component are known. Electro-active polymers include, but are not limited to, the sub-classes: piezoelectric polymers, electromechanical polymers, relaxor ferroelectric polymers, electrostrictive polymers, dielectric elastomers, liquid crystal elastomers, conjugated polymers, Ionic Polymer Metal Composites, ionic gels and polymer gels.

The sub-class electrostrictive polymers includes, but is not limited to:

Polyvinylidene fluoride (PVDF), Polyvinylidene fluoride-trifluoroethylene (PVDF-TrFE), Polyvinylidene fluoride-trifluoroethylene-chlorofluoroethylene (PVDF-TrFE-CFE), Polyvinylidene fluoride-trifluoroethylene-chlorotrifluoroethylene) (PVDF-TrFE-CTFE), Polyvinylidene fluoride-hexafluoropropylene (PVDF-HFP), polyurethanes or blends thereof.

The sub-class dielectric elastomers includes, but is not limited to:

acrylates, polyurethanes, silicones.

The sub-class conjugated polymers includes, but is not limited to:

polypyrrole, poly-3,4-ethylenedioxythiophene, poly(p-phenylene sulfide), polyanilines.

Ionic devices may be based on ionic polymer-metal composites (IPMCs) or conjugated polymers. An ionic polymer-metal composite (IPMC) is a synthetic composite nanomaterial that displays artificial muscle behavior under an applied voltage or electric field.

In more detail, IPMCs are composed of an ionic polymer like Nafion or Flemion whose surfaces are chemically plated or physically coated with conductors such as platinum or gold, or carbon-based electrodes. Under an applied voltage, ion migration and redistribution due to the imposed voltage across a strip of IPMCs result in a bending deformation. The polymer is a solvent swollen ion-exchange polymer membrane. The field causes cations travel to cathode side together with water. This leads to reorganization of hydrophilic clusters and to polymer expansion. Strain in the cathode area leads to stress in rest of the polymer matrix resulting in bending towards the anode. Reversing the applied voltage inverts the bending.

If the plated electrodes are arranged in a non-symmetric configuration, the imposed voltage can induce all kinds of deformations such as twisting, rolling, torsioning, turning, and non-symmetric bending deformation.

In all of these examples, additional passive layers may be provided for influencing the electrical and/or mechanical behavior of the EAP layer in response to an applied electric field.

The EAP component of each unit may be sandwiched between electrodes. The electrodes may be stretchable so that they follow the deformation of the EAP material. Materials suitable for the electrodes are also known, and may for example be selected from the group consisting of thin metal films, such as gold, copper, or aluminum or organic conductors such as carbon black, carbon nanotubes, graphene, poly-aniline (PANI), poly(3,4-ethylenedioxythiophene) (PEDOT), e.g. poly(3,4-ethylenedioxythiophene) poly(styrenesulfonate) (PEDOT:PSS). Metalized polyester films may also be used, such as metalized polyethylene terephthalate (PET), for example using an aluminum coating.

The invention can be applied in many EAP and photoactive polymer applications, including examples where a passive matrix array of actuators or sensors, or combined sensor and actuators is of interest.

EAP actuators for example provide unique benefits mainly because of the small form factor, the flexibility and the high energy density. Hence EAPs and photoresponsive polymers can be easily integrated in soft, 3D-shaped and/or miniature products and interfaces. Examples of such applications are:

Skin cosmetic treatments such as skin actuation devices in the form of a responsive polymer based skin patches which apply a constant or cyclic stretch to the skin in order to tension the skin or to reduce wrinkles;

Respiratory devices with a patient interface mask which has a responsive polymer based active cushion or seal, to provide an alternating normal pressure to the skin which reduces or prevents facial red marks;

Electric shavers with an adaptive shaving head. The height of the skin contacting surfaces can be adjusted using responsive polymer actuators in order to influence the balance between closeness and irritation;

Oral cleaning devices such as an air floss with a dynamic nozzle actuator to improve the reach of the spray, especially in the spaces between the teeth. Alternatively, toothbrushes may be provided with activated tufts;

Consumer electronics devices or touch panels which provide local haptic feedback via an array of responsive polymer transducers which is integrated in or near the user interface;

Catheters with a steerable tip to enable easy navigation in tortuous blood vessels.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

Any reference signs in the claims should not be construed as limiting the scope.

The invention claimed is:

1. A device for application to a receiving surface, the device comprising:
   a carrier having a carrier surface;
   an arrangement comprising:
      three or more surface interaction elements, the three or more surface interaction elements mounted to the carrier surface,
         wherein each of the three or more surface interaction elements are spatially separated from one another and distributed in two dimensions across the carrier surface;
      a first surface interaction element arranged to perform an actuation function; and
      a second surface interaction element arranged to perform a pressure sensing function; and
   a controller circuit coupled to the three or more surface interaction elements,
   wherein the controller circuit is arranged to control the first surface interaction element so as to induce a deformation in the receiving surface at a first contact point,
   wherein the controller circuit is arranged control the second surface interaction element so as to measure a pressure and/or force exerted by the receiving surface at a second contact point,
   wherein the controller circuit is arranged to determine a measure of an elasticity of the receiving surface between the first contact point and the second contact point, and
   wherein the controller circuit is arranged to control one or more third surface interaction elements to either induce a deformation in, or measure a pressure and/or force exerted by, the receiving surface at a third one or more contact points, in order thereby to enable determination of a measure of elasticity between each of the third one or more contact points, and either the second contact point or the first contact point.

2. The device as claimed in claim 1,
   wherein the controller circuit is arranged to selectively control a plurality of pairs of the three or more surface interaction elements,
   wherein each pair comprises one element arranged to perform actuation and one element arranged to perform pressure and/or force sensing, and
   wherein each element of the pair independently or simultaneously performs respective surface-deformation and pressure/force sensing functions, to thereby enable a plurality of independent or simultaneous elasticity measures across a plurality of differently angled linear sections of the receiving surface.

3. The device as claimed in claim 1, wherein the controller circuit is arranged to control one or more of the three or more surface interaction elements so as to measure a change in the pressure and/or force exerted by the receiving surface at a respective contact point following inducement of a deformation by a fourth surface interaction element at a fourth contact point.

4. The device as claimed in claim 1, wherein the controller circuit is arranged to process a plurality of pressure and/or force measurements obtained from one or more surface interaction elements, in order to enable analysis of an average or aggregate elasticity measurement for a plurality of different linear sections of the receiving surface.

5. The device as claimed in claim 1, wherein:
   a plurality of the three or more surface interaction elements are arranged to perform an actuation function,
   wherein the controller circuit is arranged to control the plurality of surface interaction elements to induce respective deformations in the receiving surface at a respective plurality of contact points,
   wherein the controller circuit is arranged to control a fifth surface interaction element to measure a pressure and/or force exerted by the receiving surface at a fifth contact point; and
      the plurality of the three or more surface interaction elements are arranged to perform a pressure and/or force sensing function,
   wherein the controller circuit is arranged to control an eleventh surface interaction element to induce a deformation in the receiving surface at an eleventh contact point, and to control the plurality of surface interaction elements to measure a pressure and/or force exerted by the receiving surface at a twelfth plurality of contact points.

6. The device as claimed in claim 5, wherein the plurality of the three or more surface interaction elements are each positioned adjacent to the fifth surface interaction element.

7. The device as claimed in claim 1, wherein at least a subset of the three or more surface interaction elements are each arranged to perform a selected one of either actuation or pressure sensing.

8. The device as claimed in claim 7, wherein the controller circuit is arranged to selectively switch each of the subset of the three or more surface interaction elements between performing an actuation function and performing a sensing function.

9. The device as claimed in claim 1,
   wherein at least a subset of the three or more surface interaction elements comprises an electroactive polymer material, and
   wherein the electroactive polymer material is arranged to deform in response to application of an electrical signal, and/or arranged to generate an electrical signal in response to a force or pressure exerted on at least one of the subset of the three or more surface interaction elements.

10. The device as claimed in claim 9,
wherein at least one surface interaction element is arranged to induce an in-plane deformation,
wherein at least an eighth surface interaction element is arranged to measure an in-plane or out-of-plane pressure and/or force,
wherein the controller circuit is arranged to apply a time-varying control signal to the at least one surface interaction element in order to control the at least one surface interaction element to induce a time-varying in-plane deformation in the receiving surface, and
wherein the controller circuit is arranged to determine, based on an output from the at least eighth surface interaction element, a time delay between generation of the time-varying deformation and detection of a pressure or force change at the at least eighth surface interaction element.

11. The device as claimed in claim 1,
wherein the controller circuit is arranged to control at least one surface interaction element to induce an out-of-plane deformation in the receiving surface at a respective contact point, and to control at least a sixth surface interaction element to measure an out-of-plane pressure and/or force exerted by the receiving surface at a sixth respective contact point, and
wherein the controller circuit is arranged to control at least one surface interaction element to induce an in-plane deformation in the receiving surface at a respective contact point, and to control at least a seventh surface interaction element to measure an in-plane or out-of-plane pressure and/or force exerted by the receiving surface at a seventh respective contact point.

12. The device as claimed in claim 11,
wherein the at least one surface interaction element is arranged to induce both an in-plane and out-of-plane deformation simultaneously, and
wherein the controller circuit is arranged to control the at least one surface interaction element to induce a non-time-varying out of plane deformation in the receiving surface.

13. The device as claimed in claim 1,
wherein the controller circuit is arranged to control the first surface interaction element to induce an out-of-plane deformation in the receiving surface, and
wherein the controller circuit is arranged to control at least a ninth surface interaction element to measure an out-of-plane pressure and/or force exerted in a direction towards the receiving surface.

14. The device as claimed in claim 13,
wherein the controller circuit is arranged to control two surface interaction elements to induce respective out-of-plane deformations in the receiving surface, and
wherein the ninth surface interaction element is positioned in-between the two surface interaction elements.

15. The device as claimed in claim 1,
wherein one or more of the three or more surface interaction elements is arranged to perform a temperature sensing function, and
wherein the controller circuit is arranged to control the one or more of the three or more surface interaction elements to measure a temperature of the receiving surface.

16. The device as claimed in claim 15, wherein the device further comprises a heating element arranged to heat the one or more of the three or more surface interaction elements and/or a portion of the receiving surface.

17. The device as claimed in claim 1, wherein the carrier is a compliant carrier for conforming to a topology of the receiving surface.

18. The device as claimed in claim 1, wherein a plurality of the three or more surface interaction elements are arranged to perform a pressure and/or force sensing function, and wherein the controller circuit is arranged to control an eleventh surface interaction element to induce a deformation in the receiving surface at an eleventh contact point, and to control the plurality of the three or more surface interaction elements to measure a pressure and/or force exerted by the receiving surface at a twelfth plurality of contact points.

19. The device as claimed in claim 1,
wherein the controller circuit is arranged to control at least one surface interaction element to induce an out-of-plane deformation in the receiving surface at a respective contact point, and to control at least a sixth surface interaction element to measure an out-of-plane pressure and/or force exerted by the receiving surface at a sixth respective contact point.

20. The device as claimed in claim 1,
wherein the controller circuit is arranged to control at least one surface interaction element to induce an in-plane deformation in the receiving surface at a respective contact point, and to control at least a seventh surface interaction element to measure an in-plane or out-of-plane pressure and/or force exerted by the receiving surface at a seventh respective contact point.

21. A method of determining a measure of elasticity of a receiving surface, the method comprising:
controlling a first surface interaction element to induce a deformation in the receiving surface at a first contact point;
controlling a second surface interaction element to measure a pressure and/or force exerted by the receiving surface at a second point, to enable determination of a measure of an elasticity of the receiving surface between the first contact point and the second contact point, wherein the first contact point is spatially separated from the second contact point; and
controlling one or more third surface interaction elements to either induce a deformation in, or measure a pressure and/or force exerted by, the receiving surface at a third one or more contact points, in order to enable determination of a third measure of elasticity between each of the third one or more points, and either the second contact point or the first contact point.

* * * * *